(12) United States Patent
Hsu et al.

(10) Patent No.: US 6,438,410 B2
(45) Date of Patent: Aug. 20, 2002

(54) SYSTEM AND METHOD FOR A CLASSIFYING CARDIAC COMPLEXES

(75) Inventors: William Hsu, Circle Pines, MN (US); Joseph Martin Smith, St. Louis, MO (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/848,605

(22) Filed: May 3, 2001

Related U.S. Application Data

(63) Continuation of application No. 09/249,128, filed on Feb. 12, 1998, now Pat. No. 6,266,554.

(51) Int. Cl.[7] ............................................. A61B 5/0452
(52) U.S. Cl. ...................................... 600/516; 600/515
(58) Field of Search .............................. 600/515, 516, 600/517, 518

(56) References Cited

U.S. PATENT DOCUMENTS

| | | | |
|---|---|---|---|
| 4,336,810 A | 6/1982 | Anderson et al. | 128/702 |
| 4,531,527 A | 7/1985 | Reinhold, Jr. et al. | 128/696 |
| 4,583,553 A | 4/1986 | Shah et al. | 128/704 |
| 4,721,114 A | 1/1988 | DuFault et al. | 128/696 |
| 4,838,278 A | 6/1989 | Wang et al. | 128/696 |
| 4,924,875 A | 5/1990 | Chamoun | 128/696 |
| 5,000,189 A | 3/1991 | Throne et al. | 128/702 |
| 5,014,284 A | 5/1991 | Langer et al. | 375/30 |
| 5,014,698 A | 5/1991 | Cohen et al. | 128/419 |
| 5,020,540 A | 6/1991 | Chamoun | 128/696 |
| 5,107,850 A | 4/1992 | Olive | 128/705 |
| 5,109,842 A | 5/1992 | Adinolfi | 128/419 |
| 5,139,028 A | 8/1992 | Steinaus et al. | 128/697 |
| 5,156,148 A | 10/1992 | Cohen | 128/419 |
| 5,184,615 A | 2/1993 | Nappholz et al. | 128/419 PG |
| 5,193,550 A | 3/1993 | Duffin | 129/697 |

(List continued on next page.)

FOREIGN PATENT DOCUMENTS

| | | | |
|---|---|---|---|
| EP | 0469817 | 2/1992 | |
| EP | 0 506 230 | 9/1992 | A61N/1/362 |
| EP | 0554208 | 8/1993 | A61B/5/0452 |
| EP | 0711531 | 5/1996 | A61B/5/0452 |
| EP | 0848965 | 6/1998 | A61N/1/37 |
| WO | 97/39681 | 4/1996 | A61B/5/046 |
| WO | WO 97/39681 | 10/1997 | A61B/5/046 |
| WO | 98/53879 | 12/1998 | A61N/1/39 |

Primary Examiner—Carl Layno
(74) Attorney, Agent, or Firm—Schwegman, Lundberg, Woessner & Kluth, P.A.

(57) ABSTRACT

A system and method classify cardiac complexes based on cardiac information derived from two or more cardiac signals. Two or more cardiac signals containing cardiac complexes are monitored. A cardiac complex in the two or more cardiac signals is isolated in an analysis window. The morphology of the cardiac complex in each of the two or more cardiac signals is then compared to the morphology of a template cardiac complex representing a predetermined cardiac condition. Based on this comparison, the cardiac complex is classified as either belonging or not belonging to the predetermined cardiac condition.

39 Claims, 11 Drawing Sheets

U.S. PATENT DOCUMENTS

| | | | |
|---|---|---|---|
| 5,215,098 A | 6/1993 | Steinhaus et al. | 128/702 |
| 5,217,021 A | 6/1993 | Steinhaus et al. | 128/702 |
| 5,240,009 A | 8/1993 | Williams | 128/702 |
| 5,247,021 A | 9/1993 | Fujisawa et al. | 525/254 |
| 5,255,186 A | 10/1993 | Steinhaus et al. | 364/413 |
| 5,269,301 A | 12/1993 | Cohen | 607/6 |
| 5,271,411 A | 12/1993 | Ripley et al. | 128/702 |
| 5,273,049 A | 12/1993 | Steinhaus et al. | 128/696 |
| 5,275,621 A | 1/1994 | Mehra | 607/5 |
| 5,280,792 A | 1/1994 | Leong et al. | 128/702 |
| 5,292,348 A | 3/1994 | Saumarez et al. | 607/5 |
| 5,311,874 A | 5/1994 | Baumann et al. | 128/705 |
| 5,312,445 A | 5/1994 | Nappholz et al. | 607/9 |
| 5,313,953 A | 5/1994 | Yomtov et al. | 128/696 |
| 5,330,504 A | 7/1994 | Somerville et al. | 607/5 |
| 5,331,966 A | 7/1994 | Bennett et al. | 128/696 |
| 5,350,406 A | 9/1994 | Nitzsche et al. | 607/14 |
| 5,360,436 A | 11/1994 | Alt et al. | 607/18 |
| 5,366,487 A | 11/1994 | Adams et al. | 607/5 |
| 5,388,578 A | 2/1995 | Yomtov et al. | 600/393 |
| 5,400,795 A | 3/1995 | Murphy et al. | 128/702 |
| 5,411,031 A | 5/1995 | Yomtov | |
| 5,421,830 A | 6/1995 | Epstein et al. | 607/30 |
| 5,447,519 A | 9/1995 | Peterson | 607/5 |
| 5,447,524 A | 9/1995 | Alt | 607/19 |
| 5,456,261 A | 10/1995 | Luczyk | 128/702 |
| 5,458,623 A | 10/1995 | Lu et al. | 607/28 |
| 5,478,807 A | 12/1995 | Cronin et al. | 514/12 |
| 5,509,927 A | 4/1996 | Epstein et al. | 607/32 |
| 5,520,191 A | 5/1996 | Karlsson | |
| 5,542,430 A | 8/1996 | Farrugia et al. | 128/705 |
| 5,622,178 A | 4/1997 | Gilham | 128/696 |
| 5,628,326 A | 5/1997 | Arand et al. | 128/706 |
| 5,634,468 A | 6/1997 | Platt et al. | 128/696 |
| 5,645,070 A | 7/1997 | Turcott | 128/702 |
| 5,682,900 A * | 11/1997 | Arand et al. | 600/517 |
| 5,683,425 A | 11/1997 | Hauptmann | 607/9 |
| 5,687,737 A | 11/1997 | Branham et al. | 128/710 |
| 5,704,365 A | 1/1998 | Albrecht et al. | 128/702 |
| 5,712,801 A | 1/1998 | Turcott | 364/550 |
| 5,713,367 A | 2/1998 | Arnold et al. | 128/704 |
| 5,724,985 A | 3/1998 | Snell et al. | 128/697 |
| 5,730,142 A | 3/1998 | Sun et al. | 128/705 |
| 5,738,105 A | 4/1998 | Kroll | 128/708 |
| 5,755,739 A | 5/1998 | Sun et al. | 607/14 |
| 5,759,158 A | 6/1998 | Swanson | 600/508 |
| 5,772,604 A | 6/1998 | Langberg et al. | 600/518 |
| 5,778,881 A | 7/1998 | Sun et al. | 128/696 |
| 5,779,645 A | 7/1998 | Olson et al. | 600/518 |
| 5,782,888 A | 7/1998 | Sun et al. | 607/27 |
| 5,792,065 A | 8/1998 | Xue et al. | 600/516 |
| 5,797,399 A | 8/1998 | Morris et al. | 128/705 |
| 5,797,849 A | 8/1998 | Vesley et al. | 600/461 |
| 5,819,007 A | 10/1998 | Elghazzawi | 395/51 |
| 5,819,741 A | 10/1998 | Karlsson | |
| 5,848,972 A | 12/1998 | Triedman et al. | 600/508 |
| 5,857,977 A | 1/1999 | Caswell et al. | 600/518 |
| 5,858,977 A | 1/1999 | Aukerman et al. | 514/12 |
| 5,935,082 A | 8/1999 | Albrecht et al. | 600/515 |
| 5,954,661 A | 9/1999 | Greenspon et al. | 600/510 |

* cited by examiner

SYSTEM AND METHOD FOR A CLASSIFYING CARDIAC COMPLEXES

CROSS REFERENCE TO RELATED APPLICATIONS

This application is a continuation of U.S. patent application Ser. No. 09/249,128, filed on Feb. 12, 1998 now U.S. Pat. No. 6,266,554, the specification of which is incorporated herein by reference.

FIELD OF THE INVENTION

This invention relates generally to the field of medical devices and more particularly to a system and method for classifying sensed cardiac complexes.

BACKGROUND

Effective, efficient ventricular pumping action depends on proper cardiac function. Proper cardiac function, in turn, relies on the synchronized contractions of the heart at regular intervals. When normal cardiac rhythm is initiated at the sinoatrial node, the heart is said to be in sinus rhythm. However, when the heart experiences irregularities in its coordinated contraction, due to electrophysiological disturbances caused by a disease process or from an electrical disturbance, the heart is denoted to be arrhythmic. The resulting cardiac arrhythmia impairs cardiac efficiency and can be a potential life threatening event.

Cardiac arrhythmias occurring in the atrial of the heart are called supraventricular tachyarrhythmias (SVTs). Cardiac arrhythmias occurring in the ventricular region of the heart are called ventricular tachyarrhythmias (VTs). SVTs and VTs are morphologically and physiologically distinct events. VTs take many forms, including ventricular fibrillation and ventricular tachycardia. Ventricular fibrillation is a condition denoted by extremely rapid, nonsynchronous contractions of the ventricles. This condition is fatal unless the heart is returned to sinus rhythm within a few minutes. Ventricular tachycardia are conditions denoted by a rapid heart beat, 150 to 250 beats per minute, that has its origin in some abnormal location within the ventricular myocardium. The abnormal location is typically results from damage to the ventricular myocardium from a myocardial infarction. Ventricular tachycardia can quickly degenerate into ventricular fibrillation.

SVTs also take many forms, including atrial fibrillation and atrial flutter. Both conditions are characterized by rapid uncoordinated contractions of the atria. Besides being hemodynamically inefficient, the rapid contractions of the atria can also adversely effect the ventricular rate. This occurs when the aberrant contractile impulse in the atria are transmitted to the ventricles. It is then possible for the aberrant atrial signals to induce VTs, such as a ventricular tachycardia.

Implantable cardioverter/defibrillators (ICDs) have been established as an effective treatment for patients with serious ventricular tachyarrhythmias. ICDs are able to recognize and treat tachyarrhythmias with a variety of tiered therapies. These tiered therapies range from providing antitachycardia pacing or cardioversion energy for treating tachycardia to defibrillation energy for treating ventricular fibrillation. To effectively deliver these treatments, the ICD must first identify the what type of tachyrhythmia is occurring in the heart.

Attempts at identifying tachyarrhythmias have included comparing the morphologies of individual cardiac complexes to model or template cardiac complexes. Template cardiac complex morphologies are created from cardiac complexes sensed from a signal channel electrogram. Once created, the template cardiac complex morphologies are integrated into morphology algorithms programmed into the ICD. As the ICD encounters a tachycardia episode, cardiac complexes sensed on the single channel electrogram are compared to the template cardiac complex morphologies in the morphology algorithms. Comparing the morphologies of each cardiac complex to the template cardiac complex requires the signals of the two complexes to be positioned over each other. The morphologies of the signals are then analyzed in a time and energy intensive signal shape analysis to determine whether the cardiac complex should be classified as a template cardiac complex.

For the reasons stated above, and for other reasons stated below which will become apparent to those skilled in the art upon reading and understanding the present specification, there is a need in the art for providing a reliable system and method for analyzing and classifying cardiac complexes in a more time and energy efficient manner.

SUMMARY OF THE INVENTION

As explained in detail below, the present subject matter utilizes cardiac information from two or more cardiac signals to analyze and classify sensed cardiac complexes in a more time and energy efficient manner. The two or more cardiac signals are sensed from two or more locations within, or on, the heart of the patient. A cardiac complex sensed using two or more cardiac signals includes the relative time at which the cardiac complex is sensed in each of the two or more cardiac signals. This additional factor allows for a more efficient comparison to be made between a sensed cardiac complex and a template cardiac complex representing a predetermined cardiac condition. Based on the comparison, the cardiac complex is classified and this information is used to either determine what type of therapy to deliver to a patient or to assess the occurrence of a variety of predetermined cardiac conditions which may be helpful in providing treatment to the patient.

In one embodiment, the present subject matter provides for the monitoring of two or more cardiac signals representative of a patient's cardiac activity. A cardiac complex is detected in each of the two or more cardiac signals, where the cardiac complex in each of the two or more cardiac signals represents at least a portion of the heart's cardiac cycle. The morphology of the cardiac complex in each of the two or more cardiac signals is then compared to the morphology of a template cardiac complex. Based on the morphology comparison, the cardiac complex is then classified as either being associated with the template cardiac complex or not being associated with the template cardiac complex.

In one embodiment, a first signal and a second signal representative of electrical cardiac activity are monitored. As the first signal is being monitored it is analyzed to detect the onset of a tachycardia episode. When a tachycardia episode is detected, individual cardiac complexes in the first signal and the second signal are detected and windowed for analysis. Predetermined features are then located in the cardiac complex detected in the first signal and in a first normal sinus rhythm representative complex. In one embodiment, the predetermined features include repeatably identifiable complex sections common to the cardiac complex detected in the first signal and the first NSR representative complex.

The predetermined features located in the first signal and in the first NSR representative complex are then aligned within the analysis window. The cardiac complex detected in the second signal is then compared to a second NSR representative complex to determine whether the cardia complex is an arrhythmic cardiac complex. In one embodiment, the morphology of the second NSR representative complex and the morphology of the cardiac complex detected in the second signal to determine whether the cardia complex is an arrhythmic complex.

In an alternative embodiment, as a cardiac complexes are detected in the first signal and the second signal they are windowed for analysis. Predetermined features are then located in the cardiac complex detected in the first signal and in a first normal sinus rhythm representative complex. Scalar values are then generated as a function of the position, or location, of the predetermined features in each of the cardiac signals. The scalar values are then used to create a cardiac vector which represents the cardiac complex.

The cardiac vector is compared to one or more classification vectors, where each of the one or more classification vectors represents a predetermined cardiac condition. A similarity coefficient is determined for the comparison between the cardiac vector and each of the one or more classification vectors. When a similarity coefficient for the comparison of the cardiac vector and a classification vector exceeds a predetermined threshold, the cardiac complex is classified as the predetermined cardiac condition represented by the classification vector.

Additionally, the cardiac vector can be aligned with a classification vector prior to comparing the two vectors. In one embodiment, the process of aligning includes adjusting each scalar value in the cardiac vector so one of the element positions of the cardiac vector equals a scalar value in a corresponding element position in a classification vector.

In an alternative embodiment, as a cardiac complexes are detected in the first signal and the second signal they are windowed for analysis. The morphology of the cardiac complex in the first cardiac signal and the second cardiac signal is then compared to a first template morphology and a second template morphology, respectively. The cardiac complex is then classified based on the comparison of the morphology of the cardiac complex in the first cardiac signal and the second cardiac signal to the first template morphology and the second template morphology.

These and other features and advantages of the invention will become apparent from the following description of the embodiments of the invention.

DETAILED DESCRIPTION

Figure 1:
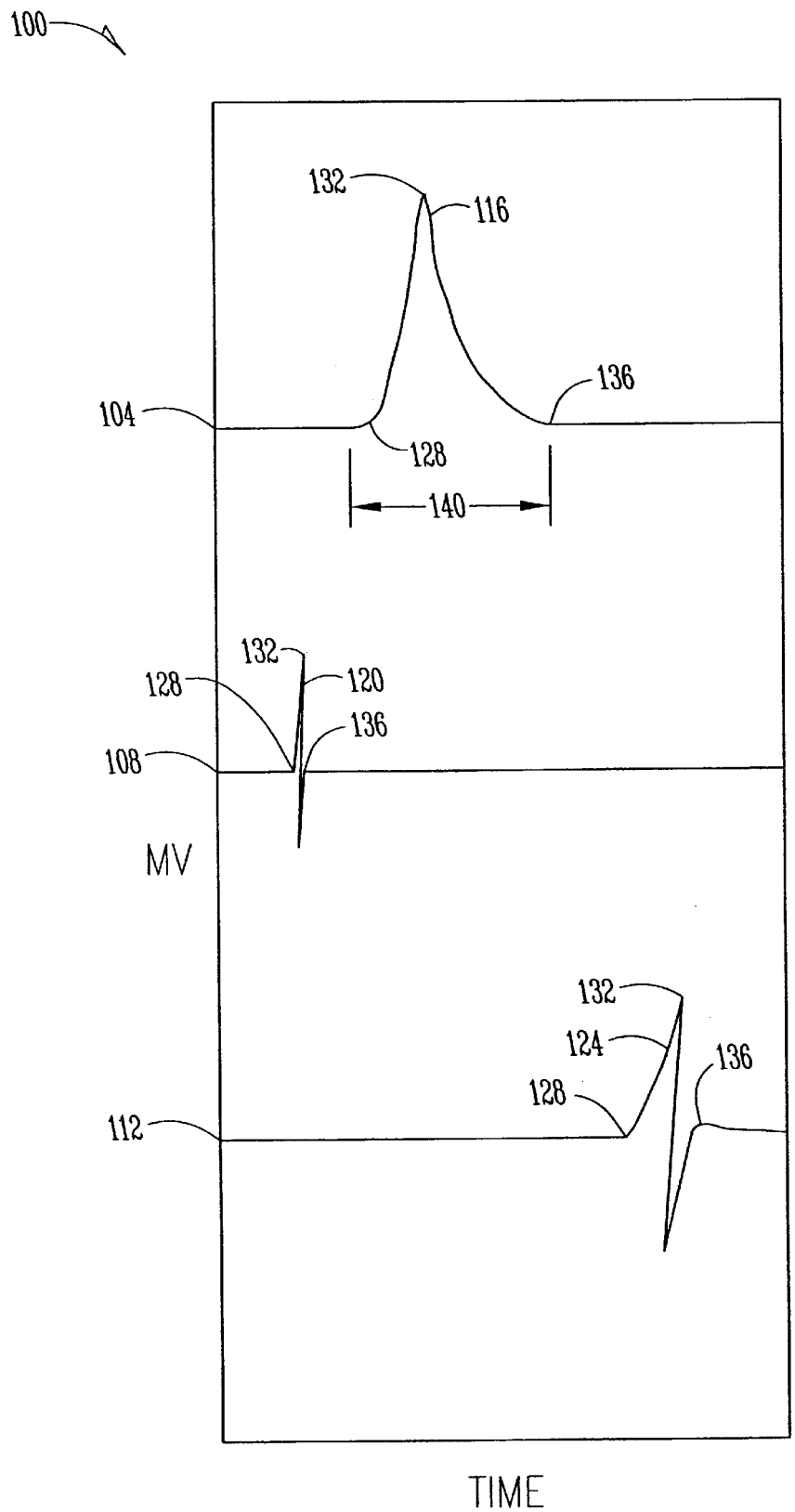
FIG. 1 is an embodiment of a cardiac complex sensed in two or more cardiac signals according to the present subject matter.

In the following detailed description, reference is made to the accompanying drawings which form a part hereof and in which is shown by way of illustration specific embodiments in which the invention may be practiced. These embodiments are described in sufficient detail to enable those skilled in the art to practice and use the invention, and it is to be understood that other embodiments may be utilized and that electrical, logical, and structural changes may be made without departing from the spirit and scope of the present invention. The following detailed description is, therefore, not to be taken in a limiting sense and the scope of the present invention is defined by the appended claims and their equivalents.

The embodiments of the present subject matter illustrated herein are described as being included in an implantable cardiac defibrillator, which may include numerous pacing modes known in the art and an external medical device programmer. In one embodiment, the implantable cardiac defibrillator is a single chamber defibrillator. In an alternative embodiment, the implantable cardiac defibrillator is a dual chamber defibrillator. Examples of both single and dual chamber implantable cardiac defibrillators are known in the art. However, the present medical system can also be implemented in an external cardioverter/monitor system as are known in the art. Also, the present medical system can also be implemented in an implantable atrial cardioverter-defibrillator, which may include numerous pacing modes known in the art. Furthermore, although the present system is described in conjunction with an implantable cardiac defibrillator having a microprocessor based architecture, it will be understood that the implantable cardiac defibrillator (or other implanted device) may be implemented in any logic based custom integrated circuit architecture, if desired.

With respect to the present subject matter, accurate classification of sensed cardiac complexes is important to an overall diagnosis and treatment of a patient's cardiac condition. In an effort to classify and catagorize sensed cardiac complexes, the morphology of individual cardiac complexes is compared to template cardiac complexes. The template cardiac complexes are derived from cardiac complexes sensed during arrhythmic or non-arrhythmic cardiac episodes.

The cardiac signals used in creating the template cardiac complex and classifying sensed cardiac complexes have typically been detected using a signal channel electrogram. Single channel electrograms, however, limit the amount of cardiac information available to use in classifying cardiac complexes. In contrast, one unique aspect of the present subject matter is that cardiac information from two or more cardiac channels is used to classify sensed cardiac complexes. Using two or more cardiac channels provides cardiac information from two or more locations within, or on, the heart of the patient. By utilizing multiple cardiac channels, cardiac information (e.g., sensed cardiac complexes) from the two or more cardiac regions and/or locations provide a larger overall and more complete "view" of the sensed cardiac complexes.

The present subject matter uses two or more electrogram channels in a process of analyzing and classifying cardiac complexes. Each electrogram channel is used to sense a cardiac signal, where the cardiac signal includes cardiac complexes representative of at least a portion of a cardiac cycle. By way of example, and not by way of limitation, portions of the cardiac cycle sensed can include, but are not limited to, P-waves, QRS-cardiac complexes, and R-waves. Other portions of the cardiac cycle, including sensed signals of the entire cardiac complex are considered useful and with the scope of the present subject matter.

In one embodiment, the present subject matter provides for two or more electrogram channels to simultaneously record cardiac complexes as they occur in the heart. As the cardiac complexes occur, each electrogram channel detects cardiac complexes representing portions of the cardiac cycle. The two or more electrogram channels are being sensed from sensors in or on different cardiac locations. While sensors may detect the electrical activity during the same portion of the cardiac cycle, having the sensors in different cardiac locations allows for cardiac information about the same cardiac complex to be gathered from a different "view" of the cardiac cycle. Each cardiac complex sensed with the two or more electrogram channels is placed in an analysis window, where the cardiac complex is isolated for analysis. In one embodiment, each cardiac complex is windowed by isolating and plotting the portions of the simultaneously sensed cardiac complex in the two or more electrogram channels as they occurred in time.

FIG. 1 shows one embodiment of a windowed cardiac complex 100. In the present example, the windowed cardiac complex 100 has a first cardiac channel 104, a second cardiac channel 108 and a third cardiac channel 112. Cardiac complexes are sensed over the first cardiac channel 104, the second cardiac channel 108 and the third cardiac channel 112, where each cardiac channel may sense a different portion of the cardiac complex (e.g, R-wave, QRS-cardiac complex, P-wave, etc.). In the present example, the windowed cardiac complex 100 has three views of a cardiac complex as sensed over the three cardiac channels. A first cardiac complex 116 is shown in cardiac signal sensed in the first cardiac channel 104. A second cardiac complex 120 is shown in cardiac signal sensed in the second cardiac channel 108. Finally, a third cardiac complex 123 is shown in cardiac signal sensed in the third cardiac channel 112. The first, second and third cardiac complex 116, 120 and 124 are representative of at least a portion of a single cardiac cycle. In one embodiment, the first, second and third cardiac complex 116, 120 and 124 are snapshots of the single cardiac cycle taken either at different locations within or on the heart and/or taken using different electrode configurations (e.g., far-field, near-field).

Cardiac information is derived from the windowed cardiac complexes. In one embodiment, information derived from the windowed cardiac complexes includes values derived or taken from one or more predetermined features on the cardiac complex sensed in each of the two or more cardiac channels. By way of example, and not by limitation, predetermined features of the cardiac complexes that are useful in deriving information include a maximum deflection of the cardiac complex, a beginning of a cardiac complex as indicated by a predetermined deviation of the cardiac signal from a baseline signal, an ending of a cardiac complex as indicated by a return of the first cardiac signal to a baseline signal and a fiducial point (the point of greatest slope along the cardiac complex signal). Other features of the cardiac complex signal are also useful for deriving information. In one embodiment, the selection criteria for these additional features of a cardiac complex is that the feature be a repeatably identifiable portion of the cardiac complex. In one embodiment, the features are selectively programmed into the medical device system.

FIG. 1 shows several examples of predetermined features of the sensed cardiac complex that are useful in deriving information. In one embodiment, a beginning of the first, second and third cardiac complex (116, 120 and 124) sensed in the first, second and third cardiac channel (104, 108 and 112), respectively, is generally shown at 128. A maximum deflection point of the first, second and third cardiac complex (116, 120 and 124) is shown generally at 132. Finally, an ending point of the first, second and third cardiac complex (116, 120 and 124) is shown generally at 136.

In one embodiment, the cardiac complexes sensed in the two or more cardiac channels are windowed with each of the signals of the cardiac complexes represented as a voltage at a function of time. FIG. 1 shows an example of the first, second and third cardiac complex (116, 120 and 124) sensed in the first, second and third cardiac channel (104, 108 and 112) being plotted as voltage as a function of time. Once the cardiac complex sensed in the two or more cardiac channels is represented in this fashion, information can be derived from the specific features of the cardiac complexes.

In one embodiment, the information derived from the cardiac complexes in each of the cardiac channels is the time the repeatably identifiable feature of the cardiac complex occurred. Alternatively, the information derived is a time difference between pairs of repeatably identifiable features on a cardiac complex sensed in one of the two or more electrogram channels. In one embodiment, a first time difference 140 is between the beginning 128 of the first cardiac complex 116 and the end 136 of the first cardiac complex. In an additional embodiment, the information derived is a time difference between pairs of repeatably identifiable features on two different cardiac complexes sensed in two electrogram channels. In a further embodiment, the information derived is a combination of the time difference between pairs of repeatably identifiable features on two different cardiac complexes sensed in two electrogram channels and the time differences from pairs of repeatably identifiable features on a cardiac complex sensed in one of the two or more electrogram channels.

Information from multiple cardiac channels can then be used to represent the cardiac complex. In one embodiment, the cardiac complex sensed in multiple cardiac channels can be numerically represented. One way of numerically representing the cardiac complex is to use scalar values derived from the cardiac signals of the cardiac complex. In one embodiment, the scalar values derived from the cardiac signals of the cardiac complex are the times repeatably identifiable features of the cardiac complex occur. Alternatively, time differences between the repeatably identifiable features, as previously described, are used to derive the scalar values. In an additional embodiment, the scalar values can be derived from a magnitude of the position of the predetermined feature for each of the two or more cardiac signals. In one embodiment, the magnitude of the position of the predetermined feature is the voltage measurement of the maximum deflection position along the cardiac signal.

The values derived for a cardiac complex are then used to create an "N" dimensional cardiac complex vector. In one embodiment, the cardiac complex vector has the form: A=[A1, A2, A3 . . . An], where each of the values A1–An represent scalar values derived from the repeatably identifiable features of the cardiac complex. The cardiac complex vector represents the cardiac complex, and is used to identify and classify the cardiac complex.

Once the cardiac complex vector has been derived from cardiac complex information taken from the two or more cardiac channels, the cardiac complex vector is compared to one or more classification vectors. In one embodiment, a classification vector represent a typical cardiac complex of a specific cardiac arrhythmia or cardiac state. For example, a classification vector can represent a ventricular tachycardia (VT) complex, where there can be one or more classification vectors to represent one or more different manifestations of ventricular tachycardia complexes. Additionally, classification vectors can represent supraventricular tachycardia (SVT) complexes, premature ventricular contraction (PVC) complexes, complexes indicating ischemic events, and any predefined representation of a cardiac complex.

In one embodiment, classification vectors are predefined classification vectors derived from cardiac complexes sensed over two or more cardiac channels for a population of patients. In one embodiment, the population of patients chosen to determine a classification vector display or manifest the cardiac condition of interest (e.g., VT, SVT, PVC). Cardiac complexes of the cardiac conditions of interest are recorded over two or more cardiac channels from the patients. Using repeatably identifiable features of the multiple cardiac signals representing each cardiac complex, classification vectors for a cardiac condition are developed. In one embodiment, cardiac complexes are sensed and recorded during Holter monitoring.

In one embodiment, the classification vectors has the form: C=[C1, C2, C3, . . . Cn], where each of the values C1–Cn represent scalar values derived from the repeatably identifiable features of the cardiac complexes. In one embodiment, each of the values C1–Cn are average values derived from repeatably identifiable features of the cardiac complexes for the patient population. In an alternative embodiment, each of the values C1–Cn are median values derived from repeatably identifiable features of the cardiac complexes for the patient population. One or more of the predetermined classification vectors can then be used in the implantable medical device to classify sensed cardiac complexes.

In an alternative embodiment, the classification vectors are derived from cardiac complexes sensed from the patient. In one embodiment, two or more cardiac signals are recorded from the patient for a predetermined length of time. In one embodiment, sensing and recording the cardiac complexes is accomplished through Holter monitoring. From the recorded cardiac complexes, classification vectors are developed as previously discussed. In an additional embodiment, classification vectors represent predefined deviations between two or more repeatably identifiable features of a cardiac complex in the two or more cardiac signals. In this embodiment, the classification vector is not representing a particular cardiac condition (e.g., VT, SVT, PVC complex) but rather is representative of a very specific cardiac condition or occurrence that the physician want to pay particular attention to. By developing and programming this type of classification vector, the physician can determine how may cardiac complexes of this particular type are occurring.

In an alternative embodiment, classification vectors are created after the medical device system has been implanted into the patient. One way to create patient specific classification vectors is to derive scalar values from predetermined features of the cardiac complexes sensed in the two or more cardiac channels. As the scalar values are determined from the first sensed cardiac complex, the medical device system determines the cardiac complex vector. The cardiac complex vector for the first cardiac complex is then classified as a first class of sensed cardiac complexes. As the second cardiac complex is sensed, the medical device system determines the cardiac complex vector A for the second cardiac complex. The cardiac complex vector A for the second cardiac complex is then compared to the cardiac complex vector A for the first cardiac complex to determine whether the second cardiac complex should be classified in the first class of sensed cardiac complexes or classified in a second class of sensed cardiac complexes.

Figure 2:
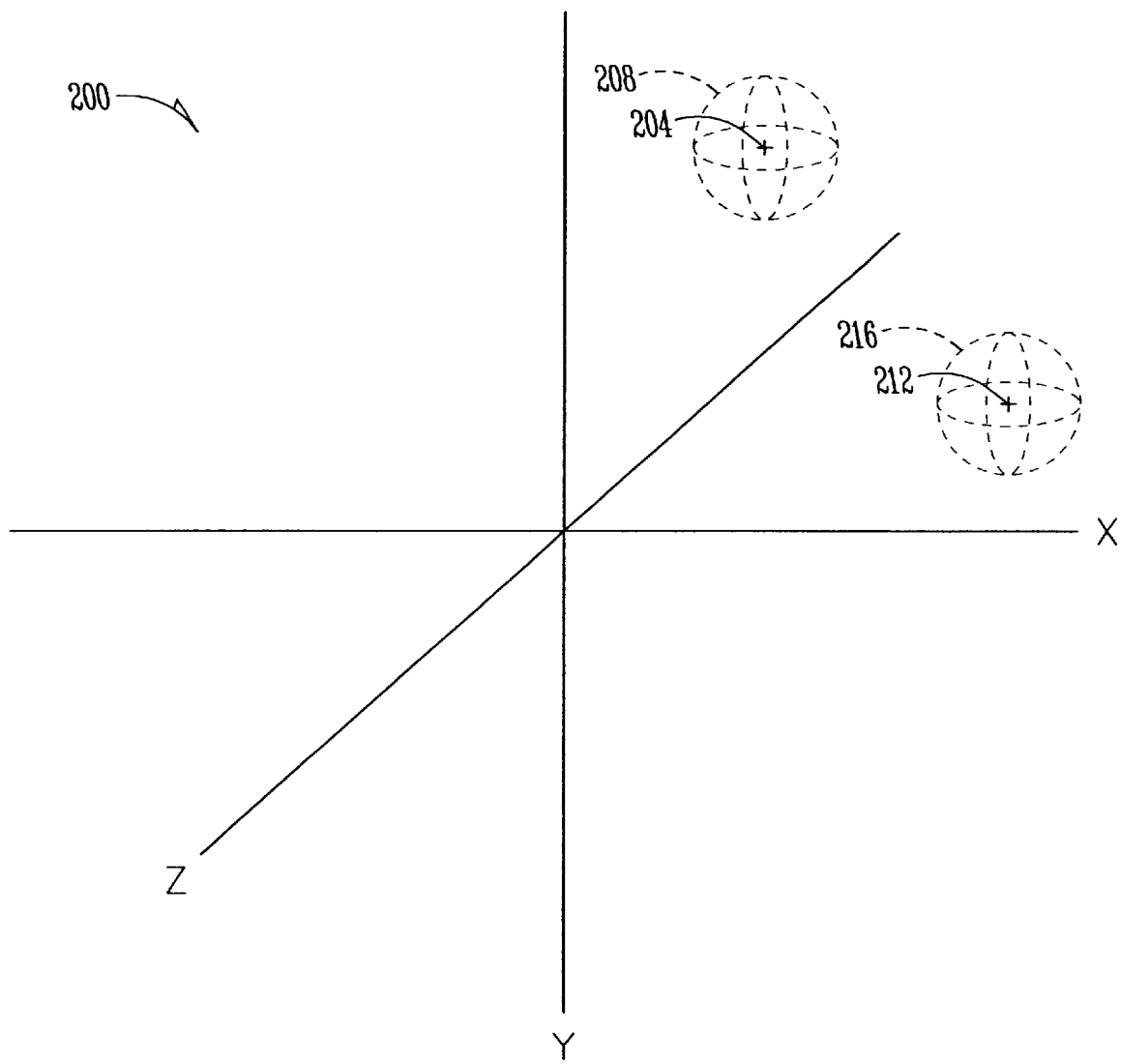
FIG. 2 is an embodiment of cardiac vectors plotted on a three-dimensional Cartesian coordinate system.

In one embodiment, determining whether a cardiac complex should be grouped with one or more classified cardiac complexes is accomplished through a process of comparing the complex vector A of the cardiac complex to be classified with the complex vector A of the cardiac complex that founded the class of cardiac complexes. FIG. 2 shows an embodiment of cardiac complex classes. FIG. 2 shows cardiac complexes being plotted in a Cartesian coordinate system with three-dimensions 200. Cardiac vectors plotted in 200 have three values A=[A1, A2, A3]. As the first cardiac complex of a patient is sensed, the cardiac vector is determined. As previously discussed, the first cardiac complex becomes the first class of sensed cardiac complexes. The cardiac vector of the first cardiac complex is shown at 204.

The cardiac vector of the first cardiac complex not only establishes the first class of sensed cardiac complexes, but it is also used to determined whether subsequently sensed cardiac complexes should be included in the first class of sensed cardiac complexes or excluded to join another class of sensed cardiac complex or form a new class of sensed cardiac complexes. In one embodiment, to determine whether a second cardiac complex is classified with the first class of sensed cardiac complexes the cardiac vector of the second cardiac complex is compared to the cardiac vector of the first cardiac complex.

In one embodiment, a mean square error calculation is used to determine if the scalar values of the cardiac vectors are sufficiently close, or within a region, or "neighborhood", to classify the second cardiac complex in the first class of cardiac complexes. In one embodiment, the mean square error is represented as $\Sigma(Ai_{(n\ class)} - Ai)^2 \leq T$, where $Ai_{(n\ class)}$ represents the ith scalar value (A1–An) of the n class (first class, second class, third class, . . . , nth class) of sensed cardiac complexes and T is a predetermined threshold value. In one embodiment, the predetermined threshold value T defines the region around the cardiac complex representing each of the classes of sensed cardiac complexes.

FIG. 2 shows one example of a first region 208 surrounding the cardiac vector of the first cardiac complex 204. As previously discussed, after the second cardiac complex is sensed, the cardiac vector representing the second cardiac complex is compared to the cardiac vector representing the first class of cardiac complexes, which in this case is the first cardiac complex 204. In one embodiment, if the cardiac vector representing the second cardiac complex falls on or within the first region 208, the second cardiac complex is classified as part of the first class of cardiac complexes.

In an alternative embodiment, if the cardiac vector representing the second cardiac complex falls outside the first region 208, the second cardiac complex is used to create a second class of cardiac complexes. In one embodiment, the cardiac vector of the second cardiac complex is shown at 212. A second region 216 surrounds the second cardiac complex 212. As previously discussed, the size of the second region 216 surrounding the second cardiac complex is dependent on the predetermined threshold value T.

As a subsequent cardiac complex is sensed a cardiac vector representing the cardiac complex is determined. The cardiac vector is then compared to each established class of cardiac complex. If the cardiac vector is found to fall within the region around a cardiac vector representing a class of cardiac complexes, the cardiac vector is classified with that class of cardiac complexes. So, if the cardiac complex is found to fall into the region representing a third class of cardiac complexes, the cardiac complex would be classified and counted with the third class of cardiac complexes. If, however, the cardiac complex does not fall into a region surrounding one or more classes of cardiac complexes, the cardiac vector of the cardiac complex is used to create a new class (an "nth" cardiac class) of cardiac complexes.

The cardiac vectors that establish a class of cardiac complexes are electronically stored in the implantable medical device. In addition to electronically storing the cardiac vectors, the medical device system also stores at least the electrocardiogram signal of the cardiac complex that established the class of cardiac complexes. In an additional embodiment, values for the cardiac vectors classified in each of the classes of cardiac complexes are also electronically stored in the medical device system. In one embodiment, it is possible that a cardiac complex is classified into two or more classes of cardiac complexes. In one embodiment, the cardiac complex falling into two or more classes of cardiac complexes will be reported in each class of cardiac complexes. In an alternative embodiment, cardiac complexes falling into two or more classes will classified and reported in the class that they were originally classified.

The patient cardiac complexes are sensed and classified by the implantable medical device for a predetermined period of time. In one embodiment, the predetermined period of time over which cardiac complexes are sensed and used to create the classes of cardiac complexes is programmed by the patient's attending physician. In one embodiment, cardiac complexes are sensed over a continuous period of time. Alternatively, the implantable medical device is programmed to classify sense cardiac complexes during predetermined time segments over the course of 24 hours. Additionally, the implantable medical device is programmed to classify sense cardiac complexes only after the cardiac rate (ventricular and/or atrial rate) has reached or exceeded are predetermined threshold (e.g., known cardiac rate threshold indicative of ventricular tachycardia, atrial tachycardia, etc.).

Upon a follow-up visit to the patient's physician, the cardiac information contained in the implantable medical device is down-loaded to a medical device programmer unit. In one embodiment, information relating to cardiac complexes used to establish classes of cardiac complexes is down-loaded and displayed on a display screen of the medical device programmer. Additionally, the number of cardiac complexes classified into each of the classes of cardiac complexes can be displayed. Electrocardiogram signals representative of each class of cardiac complex can also be displayed. The physician then uses the classes of cardiac complexes to define or designate classification vectors which are subsequently used to identify cardiac complexes and classify a cardiac arrhythmia that the patient may experience.

Figure 3:
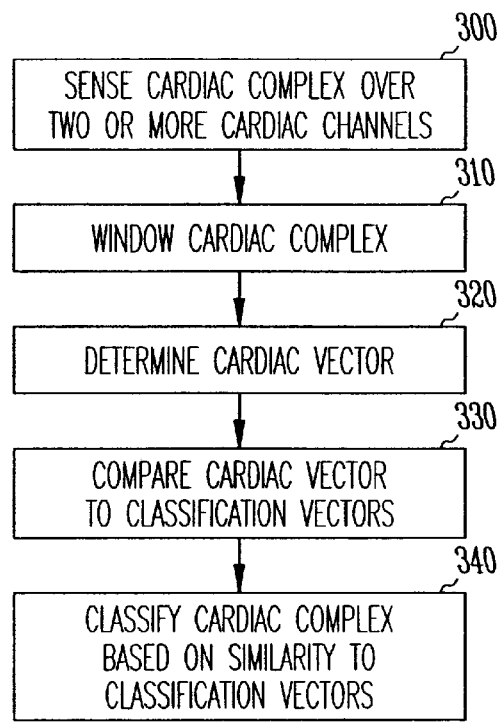
FIG. 3 is a flow diagram illustrating one embodiment of the present subject matter.

FIG. 3 shows one embodiment of a method of the present subject matter. At 300, two or more cardiac signals representative of electrical cardiac activity are monitored. The cardiac signals are monitored to detect cardiac complexes occurring in the two or more cardiac signals. In one embodiment, an implantable medical device, such as an implantable cardioverter defibrillator, is used to detect cardiac complexes in the two or more cardiac signals. In one embodiment, the implantable medical device has two or more cardiac electrodes which allow for near-field and/or far-field cardiac signals to be sensed from a heart.

At 310, the cardiac complex present in the two or more cardiac signals is isolated in an analysis window (or "windowed" for analysis). As previously discussed, windowing isolates a section, or portion, of the two or more cardiac signals which each contain a view of the cardiac complex that is being classified. After the cardiac signals containing the cardiac complex have been isolated, at least one predetermined feature is located in the cardiac complex present in each of the two or more cardiac signals.

Once the cardiac signals containing the cardiac complex have been windowed, scalar values from predetermined features of the cardiac complex are generated. In one embodiment, the scalar values are generated as a function of the position of the predetermined feature, or features, on each of the two or more cardiac signals. The scalar values are then used to create a cardiac vector, where the cardiac vector represents the cardiac complex.

Figure 4:
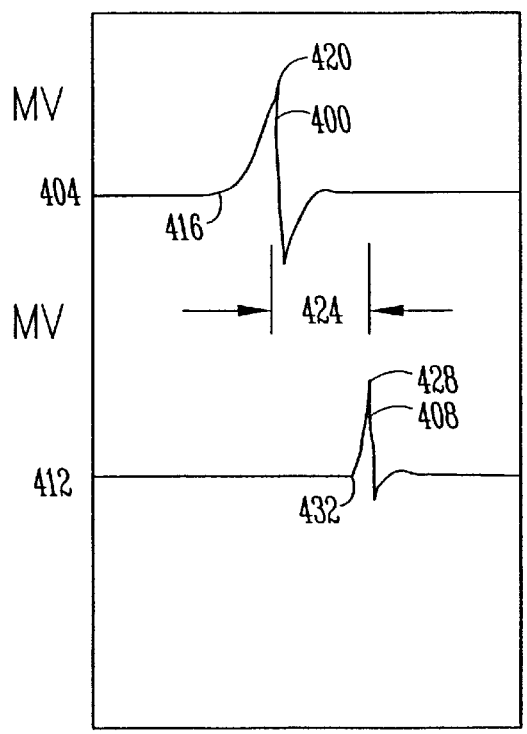
FIG. 4 is an embodiment of a cardiac complex sensed in two or more cardiac signals according to the present subject matter.

FIG. 4 shows one embodiment of cardiac complexes of a cardiac cycle windowed for analysis and classification. A first cardiac complex 400 is present in the first cardiac signal 404 and a second cardiac complex 408 is present in a second cardiac signal 412. As previously discussed, the two or more cardiac signals are sensed simultaneously from the heart, and so the first cardiac complex 400 and the second cardiac complex 408 are representative of portions of a complete cardiac cycle occurring in the heart.

Predetermined features of the cardiac complex in each cardiac signal are used to derive a cardiac vector. In the present example, the cardiac vector is programmed to have four values, such that A=[A1, A2, A3, A4]. Each of the values A1–A4 represent scalar values derived from the repeatably identifiable features of the cardiac complex. In one embodiment, A1 is programmed to be the beginning time 416 of the first cardiac complex 400, A2 is programmed to be the time of the maximum deflection point 420 of the first cardiac complex 400, A3 is programmed to be the time difference 424 between the time of the maximum deflection point 420 and the time of the maximum deflection point 428 of the second cardiac complex 408, and A4 is programmed to be the beginning time 432 of the second cardiac complex 408.

Referring again to FIG. 3, after a cardiac vector has been determined for the cardiac complex, the cardiac vector is compared to one or more classification vectors at 330. In one embodiment, the one or more classification vectors represents a predetermined cardiac condition. For example, the predetermined cardiac conditions can include, but are not limited to, ventricular and supraventricular tachycardia, PVCs, ischemia, or other predetermined cardiac conditions designated by a physician. In addition, the cardiac vector has the same vector dimension as the classification vectors. In one embodiment, the scalar values making up the cardiac vector are determined from the same relative predetermined features of the cardiac signals sensed in the same general cardiac location using the same general cardiac electrode configuration.

In one embodiment, the cardiac vector is compared to the classification vectors to determine whether the cardiac vector similar enough to one or more classification vectors to classify the cardiac complex. In one embodiment, a similarity coefficient is determined from each comparison of the cardiac vector and the one or more classification vectors. Based on this similarity coefficient, the cardiac complex is classified as the predetermined cardiac condition when the cardiac complex similarity coefficient exceed a predetermined threshold. In one embodiment, a mean square error is used to determine the similarity coefficient. In one embodiment, the mean square error value is represented as $\Sigma(Ai-Ci)^2 \leq X$, where Ai represents the ith scalar value (A1–An) of the cardiac vector, Ci represents the ith scalar value (C1–Cn) of the classification vector and X is a predetermined threshold value. In one embodiment, the predetermined threshold value X defines the region or a neighborhood around the classification vector which is deemed to be sufficiently close to permit classifying the cardiac complex represented by the cardiac vector as a general class of cardiac complexes represented by the classification vector. Based on the comparison, the cardiac complex is classified at 340 as being a member of the group represented by one or more classification vectors if possible.

In an additional embodiment, prior to comparing the cardiac vector to the classification vectors, the cardiac vector is aligned, or coordinated with, each of the classification vectors. In one embodiment, the cardiac vector and the classification vectors include element positions (A1 and C1 are in the first element position, A2 and C2 are in the second element position, etc.) which are occupied by the scalar values. The cardiac vector and a classification vector are aligned around the scalar values in the same element position (i.e., a coordinating element position) in both the cardiac vector and the classification vector.

In one embodiment, the process of aligning the cardiac vector and the classification vector involves adjusting each scalar value of the cardiac vector so one of the element positions of the cardiac vector equals a scalar value in a corresponding element position in a classification vector. So, when the scalar values in the vectors are the time of occurrence of features in different channels, the vectors are aligned by add or subtract an appropriate numerical value to all the elements of the cardiac vector (e.g., the scalar values in the cardiac vector) so that the scalar value in the coordinating element position of the cardiac vector has the same numerical value as the coordinating element position of the classification vector.

In one embodiment of aligning a cardiac vector and a classification vector, a cardiac complex is sensed two or more cardiac channels, from which a cardiac vector A=[A1, A2, A3, A4] is determined. In this embodiment, the elements of the vector are times at which the repeatably identifiable features of the cardiac complex occurred in the two or more cardiac channels. One or more classification vectors are provided having the general form C=[C1, C2, C3, C4]. In one embodiment, the cardiac vector is aligned, or coordinated, around the same element position (the coordinating element) with each classification vector the cardiac vector is compared with. In one embodiment, the coordinating element is the first position in the cardiac vector and the classifying vector, A1 and C1. A numerical value Y is added to, or subtracted from, the value of A1 so that A1 equals C1. So, A1+Y=C1, where Y can have either a positive or a negative numerical value. In addition to modifying the value of A1 with Y, Y is also added to the remaining elements of the cardiac vector. So, a cardiac vector aligned with a classification vector has the form $A_a$=[A1+Y, A2+Y, A3+Y, A4+Y], where A1+Y=C1 of the classification vector C=[C1, C2, C3, C4]. After the cardiac vector has been aligned with the classification vector, the elements of the vectors, excluding the coordinating elements, are compared. This means that for the present example, the classification vector $A_a$=[A2+Y, A3+Y, A4+Y] would be compared to the classification vector C=[C2, C3, C4]. Finally, the cardiac vector can be aligned with a classification vector around any element (e.g., A1/C1, A2/C2, etc.) in the pair of vectors.

As previously discussed, the present subject matter uses two or more electrogram channels in a process of analyzing and classifying cardiac complexes. In one embodiment, a first cardiac signal and a second cardiac signal are sensed over a first electrogram channel and a second electrogram channel, respectively. During a tachycardia episode, a cardiac complex is detected in the first cardiac signal and the second cardiac signal. The morphology of the first cardiac signal and the second cardiac signal representing the cardiac complex can then be compared to template cardiac complexes. Based on this comparison, the cardiac complex can be classified as being representative of one or more predetermined cardiac rhythm states. Predetermined cardiac rhythm states can include, but are not limited to, arrhythmic or non-arrhythmic, normal sinus rhythm (NSR), ventricular tachycardia and/or supraventricular tachycardia cardiac rhythm states.

In an additional embodiment, the process of comparing the morphology of the cardiac complex to a template cardiac complex includes the act of aligning, or coordinating, the cardiac complex sensed in a first cardiac signal of the two or more cardiac signals with a template cardiac complex having been derived from cardiac complexes sensed in the first cardiac signal. Alternatively, the morphology of the cardiac complex sensed in the two or more cardiac channels is compared to the morphology of the template cardiac complex which was derived from cardiac complexes sensed in the two or more cardiac channels.

In one embodiment, a first cardiac signal and a second cardiac signal are sensed over a first electrogram channel and a second electrogram channel, respectively. During a tachycardia episode, a cardiac complex is detected in the first cardiac signal and the second cardiac signal. In one embodiment, the cardiac complex detected in the first cardiac signal is aligned, or coordinated, with a first normal sinus rhythm (NSR) representative complex. In one embodiment, the first NSR representative complex is the template cardiac complex which, in the present embodiment, was derived from normal sinus rhythm cardiac complexes detected in the first cardiac signal.

Once the cardiac complex from the first cardiac signal has been aligned with the first NSR representative complex, the cardiac complex from the second cardiac signal is morphologically compared to the second NSR representative complex. In the present embodiment, this comparison is then used to classify the cardiac complex as either a complex representative of an arrhythmic episode or of a non-arrhythmic episode.

Through the process of first aligning the cardiac complex sensed in the first cardiac signal with the first NSR representative complex, the comparison of the cardiac complex as sensed in the second cardiac signal to the second NSR representative complex not only uses the relative morphologies of the cardiac complexes in classifying the cardiac complex, but also takes into consideration the relative time the cardiac complex detected in the first cardiac signal occurred with respect to the cardiac complex detected in the second cardiac signal. The relative time between the sensed cardiac complex in the first cardiac signal and the second cardiac signal helps to further accentuates morphological differences in the cardiac complex and template cardiac complex.

Figure 5:
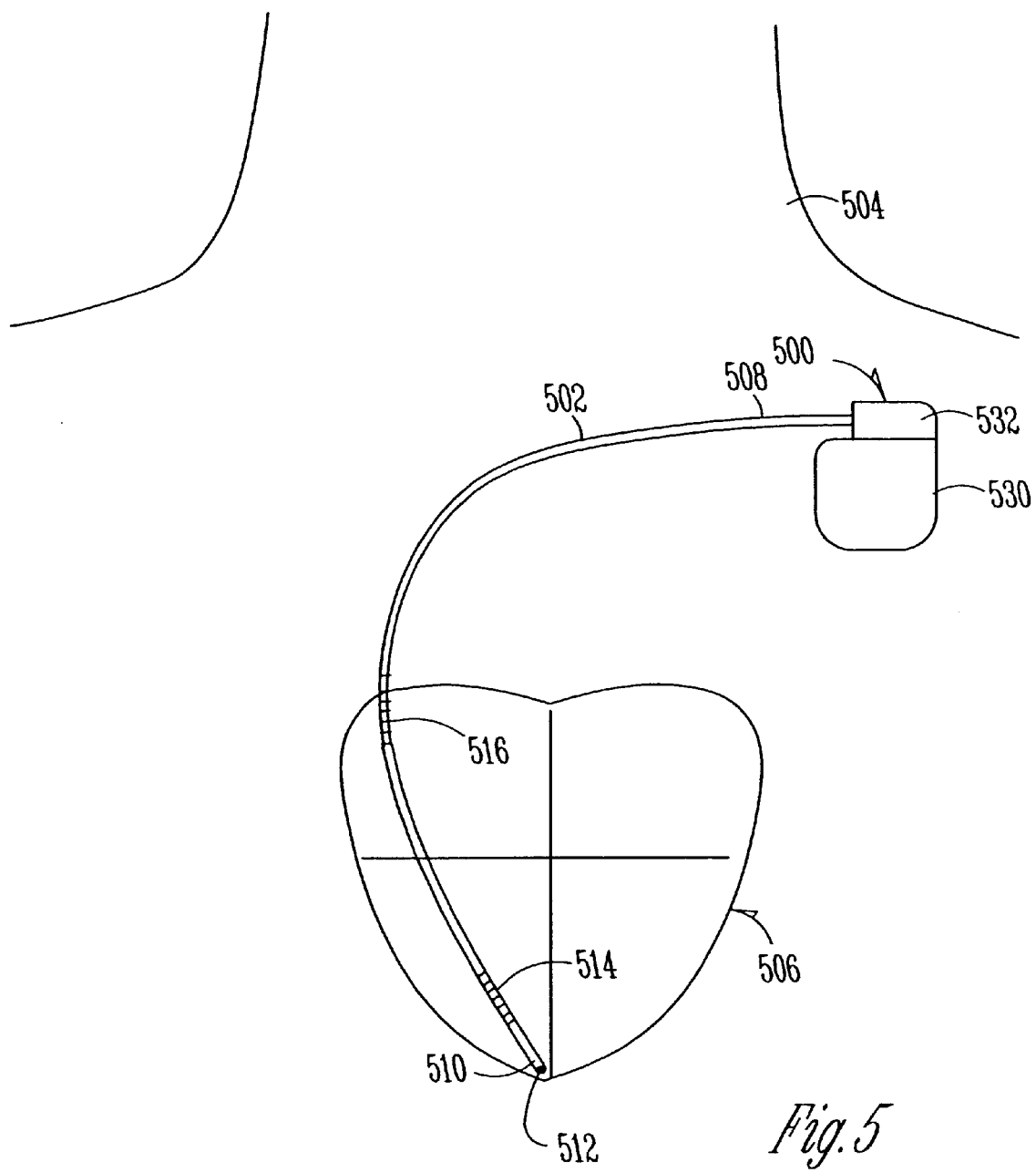
FIG. 5 is a schematic view of one embodiment of an implantable medical device with an endocardial lead implanted in a heart from which segments have been removed to show details.

Referring now to FIG. 5 of the drawings, there is shown one embodiment of a medical device system suitable for implementing the present subject matter. By way of example only, and not by limitation, the medical device system includes an implantable cardiac defibrillator 500 electrically and physically coupled to at least one catheter 502. In one embodiment, the catheter 502 is an intracardiac catheter which includes at least a first cardiac electrode and a second cardiac electrode.

The catheter 502 is implanted in a human body 504 with portions of the catheter 502 inserted into a heart 506 to detect and analyze electric cardiac signals produced by the heart 506 and to provide electrical energy to the heart 506 under certain predetermined conditions to treat cardia arrhythmias, including ventricular fibrillation, of the heart 506.

In one embodiment, the catheter 502 is an endocardial lead adapted to be releasably attached to the cardiac defibrillator 500. The catheter 502 has an elongate body with a proximal end 508 and a distal end 510, and includes at least a first cardiac electrode and a second cardiac electrode. In one embodiment, the catheter 502 has a pacing electrode 512 located at, or adjacent, the distal end 510 of the catheter 502. Additional pacing electrodes can also be included on the catheter 502 to allow for bipolar sensing and pacing with the pacing electrode 512. In addition, other pacing and sensing electrode configurations are also possible. The catheter 502 also includes one or more defibrillation electrodes. In one embodiment, the catheter 502 has a first defibrillation electrode 514 and a second defibrillation electrode 516, where the defibrillation electrodes have a coil construction as is known.

In addition to the catheter configuration shown in FIG. 5, it is considered within the scope of the present subject matter that additional catheters positioned in or around the ventricular and/or the atrial chambers can be added to the cardiac defibrillator 500 to allow for additional cardiac signals to be sensed (e.g., two or more cardiac signals). Thus, it would be possible to sense cardiac signals from any combination or subcombination of ventricular, right ventricular, left ventricular, atrial, right atria and/or left atria locations. These signals can include, but are not limited to, far-field and/or near-field cardiac signals.

Figure 6:
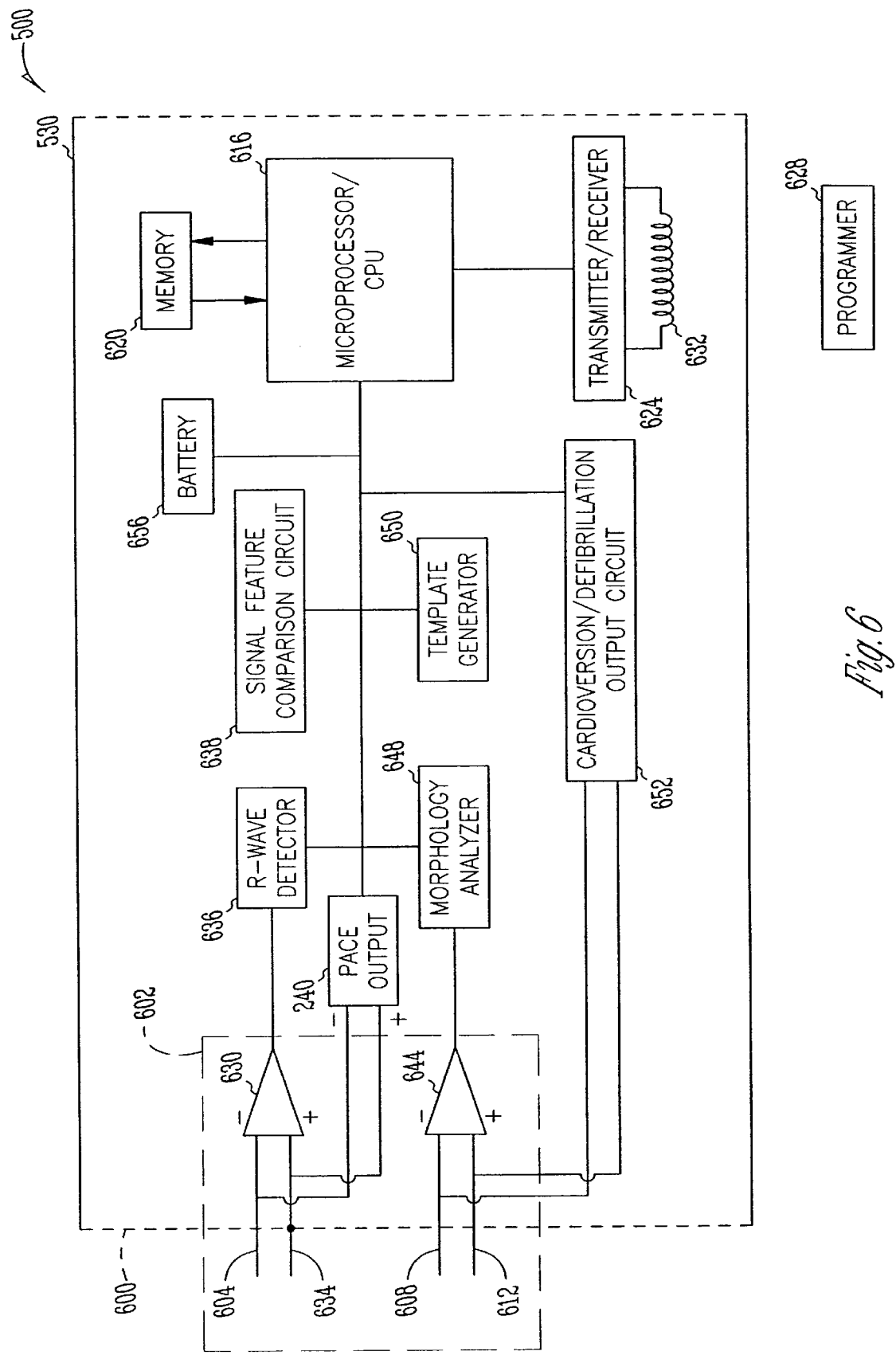
FIG. 6 is a block diagram of an implantable medical device according to one embodiment of the present subject matter.

Referring now to FIG. 6, there is shown an embodiment of a block diagram of a cardiac defibrillator 500. The cardiac defibrillator 500 includes control system circuitry 600 for receiving cardiac signals from a heart 506 and delivering electrical energy to the heart 506. The control system circuitry 600 includes a sensing system 602 attached to at least one catheter. The sensing system 602 includes terminals labeled with reference numbers 604, 608, and 612 for connection to electrodes attached to the surface of the catheter 502. In one embodiment, the pacing electrode 512 is electrically connected to terminal 604 and to the control system circuitry 600 through an electrically insulated conductor provided within the elongate body of the catheter 502. The first defibrillation electrode 514 and the second defibrillation electrode 516 are connected to terminals 608 and 612, respectively, and to the control system circuitry 600 through electrically insulated conductors provided within the elongate body of the catheter 502.

In one embodiment, the control system circuitry 600 of the cardiac defibrillator 500 is encased and hermetically sealed in a housing 530 suitable for implanting in a human body as are known in the art. A connector block 532 (FIG. 5) is additionally attached to the housing 530 of the cardiac defibrillator 500 to allow for the physical and the electrical attachment of the catheter 502 and the electrodes to the cardiac defibrillator 500 and the encased control system circuitry 600.

In one embodiment, the control system circuitry 600 of the cardiac defibrillator 500 is a programmable microprocessor-based system, with a microprocessor 616 and a memory circuit 620 which contains parameters for various pacing, defibrillation, and sensing modes and stores data indicative of cardiac signals received by the control system circuitry 600. A transmitter circuit 624 is additionally coupled to the control system circuitry 600 and the memory circuit 620 to allow the cardiac defibrillator 500 to communicate with and receive programming instructions and transmit data to and from a programmer unit 228 as is known in the art. In one embodiment, the transmitter circuit 624 and the programmer unit 628 use a wire loop antenna 632 and a radio frequency telemetric link, as is known in the art, to receive and transmit signals and data to and from the programmer unit 628 and the control system circuitry 600. In this manner, programming commands or instructions are transferred to the microprocessor 616 of the cardiac defibrillator 500 after implant, and stored cardiac data pertaining to sensed arrhythmic episodes within the heart 506 and subsequent therapy, or therapies, applied to correct the sensed arrhythmic event are transferred to the programmer unit 628 from the cardiac defibrillator 500.

In the present embodiment, the medical device system senses at least a first signal and a second signal, both of which are representative of electrical cardiac activity. The first signal and the second signal each contain cardiac complexes which represent at least a portion of the cardiac cycle. Based on the embodiment shown in FIG. 5, the first signal is a rate signal sensed within the right ventricle chamber of the heart and the second signal is a morphology signal sensed across at least a portion of the ventricular region of the heart. In an alternative embodiment, the first and second signals can be rate and morphology signals sensed in a supraventricular region of the heart. Alternatively, cardiac electrodes and/or catheters can be provided to allow for the first signal to be a morphology signal and the second signal to be a rate signal.

In the embodiment shown in FIG. 5, the pacing electrode 512 is included in a near-field channel which senses near-field signals or rate-signals of the heart 506. The near-field sensing channel includes the pacing electrode 512 which is coupled to a sense amplifier 630 within the sensing system 602. In one embodiment, the housing 530 of the cardiac defibrillator 500 is coupled to the sense amplified 630 at 634 to allow for unipolar cardiac rate sensing between the pacing electrode 512 and the housing 530 of the cardiac defibrillator 500. In an alternative embodiment, the cardiac rate signal is sensed using pacing electrode 512 and the first defibrillation electrode 514.

The output of the sense amplifier 630 is shown connected to an R-wave detector 636. The R-wave detector 636 serves to sense and amplify cardiac signals, including cardiac complexes, sensed from the heart, and apply signals indicative thereof to a signal feature comparison circuit 638. The signal feature comparison circuit 638 is coupled to the microprocessor 616. Among other things, microprocessor 616 responds to signals from the R-wave detector 636 by providing pacing signals to a pace output circuit 640, as needed according to the programmed pacing mode. In one embodiment, the pace output circuit 640 provides output pacing signals to terminals 604 and 634, which connect to the pacing electrode 512 and the housing 530 of the cardiac defibrillator 500, for cardiac pacing.

Referring again to the embodiment in FIG. 5, far-field or morphology signals are sensed through the first defibrillation electrode 514 and the second defibrillation electrode 516. The first defibrillation electrode 514 and the second defibrillation electrode 516 are used in a far-field sensing channel, where the first defibrillation electrode 514 and the second defibrillation electrode 516 are coupled to a sense amplifier 644 to sense far-field signals, which include cardiac complexes, from the heart. In an alternative embodiment, far-field signals are sensed between the first defibrillation electrode 514, the second defibrillation electrode 516 and the housing 530. The output of the sense amplifier 644 is coupled to a morphology analyzer circuit 648.

The morphology analyzer circuit 648 receives and processes the cardiac complexes detected within the cardiac signals. In one embodiment, the morphology analyzer circuit 648 receives cardiac signals, including cardiac complexes representative of the cardiac cycle from the sensing system. Cardiac complexes analyzed by the morphology analyzer circuit 648 can include detected P-waves, QRS-complexes, and R-waves. In one embodiment, the morphology analyzer circuit 648 includes an analog filter for filtering cardiac signal noise sensed by the electrodes. The cardiac signals are then bandlimited before arriving at an analog-to-digital filter which converts the analog signals into digital signals suitable for processing. In an alternative embodiment, the cardiac signals are filtered through an analog peak detector to extract the maximum and minimum cardiac signal values for each sensed cardiac complex.

In processing sensed cardiac complexes, the morphology analyzer circuit 648 windows a cardiac complex sensed in two or more cardiac signals. In one embodiment, the morphology analyzer circuit 648 locates and extracts information from one or more predetermined features of sensed cardiac complexes. As previously discussed, the type of information extracted by the morphology analyzer circuit 648 can include the time of occurrence of a predetermined feature and the amplitude value of a predetermined feature. In one embodiment, the predetermined features include repeatably identifiable portions of cardiac complexes which are repeatably identifiable in subsequent cardiac complexes. For example, features include a maximum deflection of the cardiac complex, a beginning of a cardiac complex as indicated by a predetermined deviation of the cardiac signal from a baseline signal, and an ending of a cardiac complex as indicated by a return of the first cardiac signal to a baseline signal. In one embodiment, the features are electively programmed into the medical device system.

A template generator circuit 650 is coupled to the sensing system 602. The template generator circuit 650 receives information from the morphology analyzer 648. In one embodiment, the information received from the morphology analyzer 648 includes the information extracted from the two or more cardiac signals by the morphology analyzer circuit 648. In one embodiment, the template generator circuit 650 creates the numerical representation of sensed cardiac complexes. The template generator circuit 650 then creates the "N" dimensional cardiac complex vector from these values as previously described. In addition, the template generator circuit 650 is also used to create the one or more classification vectors from a patient's own cardiac complexes as previously described.

In an alternative embodiment, the template generator circuit 650 receives at least the first signal and the second signal sensed from the heart 506. In one embodiment, the template generator circuit 650 determines a first normal sinus rhythm (NSR) representative complex and a second NSR representative complex from a plurality cardiac complexes sensed during normal sinus rhythm. In one embodiment, the first NSR representative complex and the second NSR representative complex are averages of cardiac complexes sensed in the first signal and the second signal during a patient's normal sinus rhythm. In an alternative embodiment, the first NSR representative complex and the second NSR representative complex are median values of the cardiac complexes sensed in the first signal and the second signal during a patient's normal sinus rhythm.

After the cardiac signals and information relating to the cardiac complexes in the cardiac signals have been processed by the morphology analyzer circuit 648 and the template generator circuit 650, the signals are received by a signal feature comparison circuit 638. The signal feature comparison circuit 638 uses information contained in the cardiac signals to analyze and classify sensed cardiac complexes.

In one embodiment, the signal feature comparison circuit 638 uses the one or more classification vectors which are stored in memory 620. The signal feature comparison circuit 638 compares the cardiac complex vector to the one or more classification vectors, as previously described, to classify the cardiac complex represented by the cardiac complex vector. In an additional embodiment, the signal feature comparison circuit 638 can also align the cardiac vectors with classification vectors prior to comparing the vectors when programmed to perform this function.

In an alternative embodiment, as cardiac complexes are sensed using the first cardiac signal and the second cardiac signal, the signal feature comparison circuit 638 aligns the predetermined feature in the cardiac complex monitored in the first signal with the predetermined feature on the first NSR representative complex. Once the predetermined features in the cardiac complex from the first signal is aligned with the corresponding predetermined feature in the first NSR representative complex, the morphology analyzer circuit 648 compares the cardiac complex monitored in the second signal to the second NSR representative complex to determine whether the cardiac complex is an arrhythmic complex. In one embodiment, the morphology analyzer circuit 648 compares the morphology of the cardiac complex monitored in the second signal to the second NSR representative complex to determine whether the cardiac complex is an arrhythmic complex.

In an alternative embodiment, the morphology analyzer 648 can also compare the morphology of a cardiac complex sensed in two or more cardiac channels to one or more template cardiac complexes to classify the cardiac complex. In one embodiment, the template cardiac complexes are determined from cardiac complexes sensed in the two or more cardiac channels which are subsequently used to sense cardiac complexes to be classified. Alternatively, the template cardiac complexes are determined from cardiac complexes sensed from a patient population experiencing the cardiac state for which template cardiac complexes are developed. In one embodiment, the cardiac states for which template cardiac complexes can be developed include cardiac rhythms where the left chamber and the right chamber of the ventricles or atria differ by about 20 milliseconds or more, premature ventricular contractions, ischemia, predetermined or custom patterns or classes of complexes predetermined by a physician, arrhythmia, non-arrhythmia, ventricular or supraventricular tachycardia.

In one embodiment, as sensed cardiac complexes are sensed and classified, the microprocessor 616 determines the percentage of classified cardiac complexes for a plurality of sensed cardiac complexes. In one embodiment, the microprocessor 616 determines the percentage of cardiac complexes classified as arrhythmic complexes for a plurality of cardiac complexes sensed during an arrhythmic episode. In one embodiment, once the percentage of classified cardiac complexes reaches a predetermined threshold for any one of the cardiac conditions or states programmed into the medical device system, the microprocessor 616 responds by providing signals to cardioversion/defibrillation output circuitry 652 to deliver either cardioversion or defibrillation therapy to the heart 506. Power to the cardiac defibrillator 500 is supplied by an electrochemical battery 656 that is housed within the cardiac defibrillator 500.

In addition to the catheter 502, it is possible to add additional electrodes, catheters and the accompanying required circuitry to the medical device system. For example, the cardiac defibrillator 500 can be equipped with electrodes on the surface of the housing 530 to sense surface like cardiac signals. In addition, the medical device system can further include an additional intracardiac catheter implanted in the supraventricular region of the heart. The additional intracardiac catheter includes at least one pacing electrode from which rate signals, or near field signals, from the atria are sensed and pacing pulses are delivered to pace the atrial chamber of the patient's heart. In an additional embodiment, the additional intracardiac catheter is implanted through the coronary sinus vein and down the great cardiac vein to position an electrode, such as a pacing electrode, adjacent to the left ventricular chamber of the heart.

In an alternative embodiment, the catheter 502 is implanted the supraventricular region of the heart for sensing or monitoring cardiac signals from the patient's atrial regions. In one embodiment, a pacing electrode at or adjacent the distal end of the intracardiac catheter is implanted in the coronary sinus vein to allow for rate signals to be sensed from the left atrium. In addition, far-field signals, or morphology signals, are sensed from the supraventricular region of the heart through the first defibrillation electrode and the second defibrillation electrode. In addition to implanting the catheter 502 in the supraventricular region of the heart, an additional atrial catheter can be implanted into the supraventricular region of the heart to allow for additional rate signals, or near-field signals, to be sensed along with the rate signals and morphology signals sensed with the catheter 502. Other intracardiac catheter arrangements and configurations known in the art are also possible and considered to be within the scope of the present system.

Figure 7:
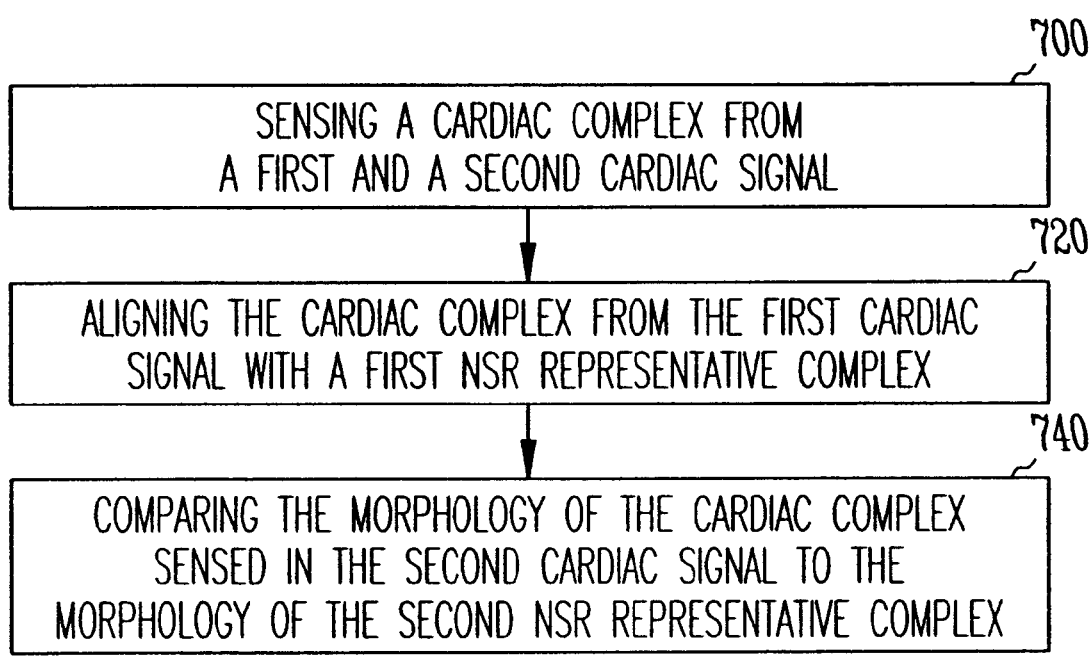
FIG. 7 is a flow diagram illustrating one embodiment of the present subject matter.

Referring now to FIG. 7, there is shown an additional embodiment of the present subject matter. At step 700, a cardiac complex is detected during a tachycardia episode in the first signal and the second signal. In one embodiment, tachycardia episodes include, but are not limited to, ventricular tachycardias and supraventricular tachycardias. In one embodiment, the medical device system analyzes at least the cardiac complexes detected in the first signal to determined the occurrence of a tachycardia episode which will be classified by the present subject matter.

In one embodiment, the first signal and the second signal detect the occurrence of cardiac cycles through either a near-field sensing channel or a far-field sensing channel as previously discussed. Cardiac complexes sensed in the first signal and the second signals can include the QRS-wave, the R-wave and/or the P-wave of the cardiac complex. This list, however, is not to be take in a limiting sense as it is recognized that other portions of the cardiac complex can also be sensed and used with the present subject matter.

As the cardiac complex is detected in the first signal and the second signal during the tachycardia episode, the first and second signal of the cardiac complex are windowed together so the cardiac complex in the first signal is positioned relative the cardiac complex in the second signal. In other words, the first signal and the second signal for each sensed tachycardiac cardiac complex are positioned relative each other according to their occurrence in time.

Figure 8A:
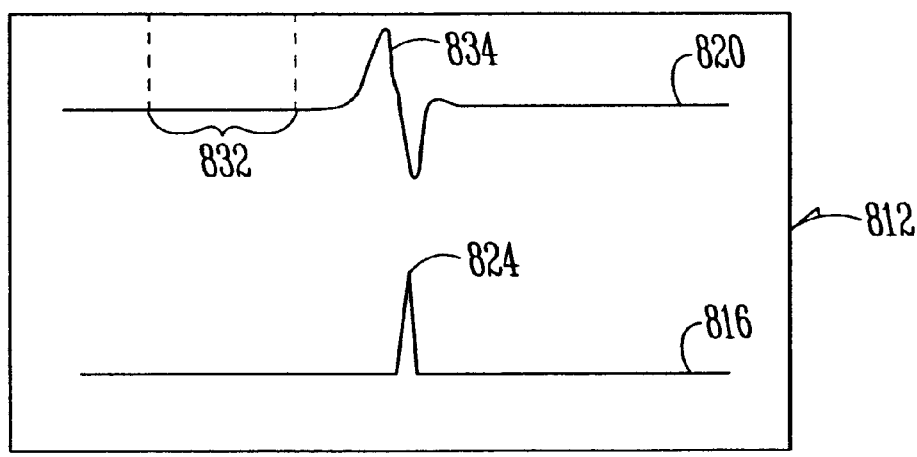
FIGS. 8A and 8B show one embodiment of aligning cardiac complexes according to the present subject matter.
Figure 8B:
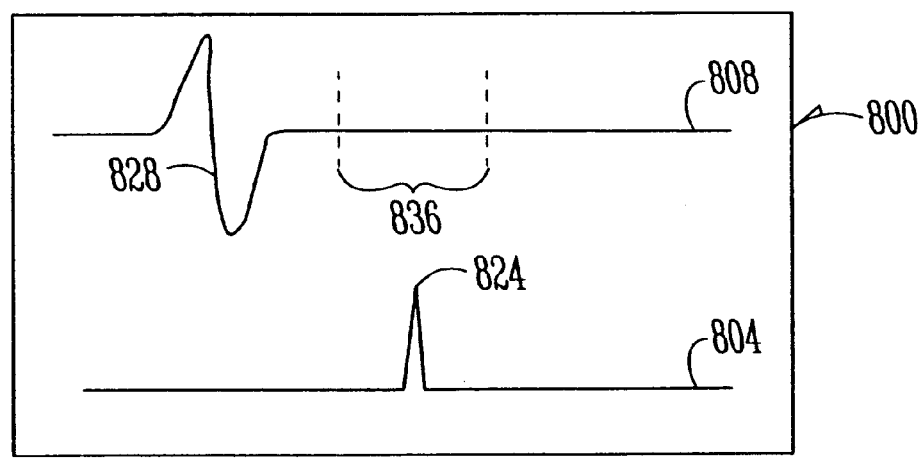

FIG. 8B shows an example of a cardiac complex having been windowed at 800. In the example, 804 shows a tachycardiac cardiac complex monitored on a near-field sensing channel, while 808 shows the cardiac complex monitored on a far-field sensing channel.

After the cardiac complex has been windowed, the first and second signals of the cardiac complex are positioned or aligned relative the first NSR representative complex and the second NSR representative complex. In one embodiment, the first and second NSR representative complexes are determined from a plurality of NSR cardiac complexes detected in the first signal and the second signal, respectively, using the same medical device system that is subsequently used to senses the cardiac complexes. In one embodiment, the first NSR representative complex and the second NSR representative complex are derived by averaging cardiac complexes detected in the first and second signals for the plurality of NSR cardiac complexes sensed from the patient. In an alternative embodiment, the first NSR representative complex and the second NSR representative complex are derived by taking a median of cardiac complexes detected in the first and second signals for the plurality of NSR cardiac complexes sensed from the patient.

In addition, the first NSR representative complex and the second NSR representative complex can be updated, either manually or automatically, to reflect changes in a patient's cardiac condition or in the medical device system. For example, the first NSR representative complex and the second NSR representative complex could change due to the type of drug or dosage of drugs being delivered to the patient and the cardiac disease state of the patient. Therefore, the system can recompute the first NSR representative complex and the second NSR representative complex at regular intervals based either on the physician's judgement or on the implantable medical devices assessment of the template. Additionally, a safe-check algorithm can be used in conjunction with any automatic updating procedure to ensure that only normal sinus rhythm complexes are used in updating the template.

At 720, the cardiac complex detected in the first signal is aligned with the first NSR representative complex. In one embodiment, the cardiac complex in the first signal and the first NSR representative complex are aligned around a predetermined feature located in the cardiac complexes. In one embodiment, the predetermined feature includes a repeatably identifiable section, or portion, of the detected cardiac complex that is common to the cardiac complex detected in the first signal and the first NSR representative complex. In one embodiment, the repeatably identifiable complex section common to the cardiac complex detected in the first signal and the first NSR representative complex is a maximum deflection of the first signal. In one embodiment, the maximum deflection is along an R-wave sensed in the cardiac complex detected in the first signal and in the first NSR representative complex.

In an alternative embodiment, the repeatably identifiable complex section common to the cardiac complex detected in the first signal and the first NSR representative complex is a predetermined deviation of the first signal from a baseline signal indicating a beginning of the cardiac complex and the first NSR representative complex. In an additional embodiment, the repeatably identifiable complex section common to the cardiac complex detected in the first signal and the first NSR representative complex is a return of the first signal to a baseline signal for each of the cardiac complex and the first NSR representative complex for a predetermined time period indicating an ending of the cardiac complex and the first NSR representative complex.

After the cardiac complex detected in the first signal has been aligned with the first NSR representative complex, the cardiac complex detected in the second signal is compared to the second NSR representative complex to determine whether the cardia complex is an arrhythmic complex. One way of determining whether the cardia complex is an arrhythmic complex is to compare the morphology of the second signal to the second NSR representative complex. In one embodiment, the second NSR representative complex has a second NSR morphology and the cardiac complex detected in the second signal has a second signal morphology. The second NSR morphology of the second NSR representative complex is then compared to the second signal morphology of the second signal to determine whether the cardia complex is an arrhythmic complex. A variety of techniques exist for morphologic analysis of sensed cardiac complexes. In one embodiment, the morphology of the cardiac complex sensed in second signal and the morphology of the second NSR representative complex are compared using a correlation waveform analysis, as is known in the art. In addition to correlation waveform analysis, other morphology comparison methods or methods of classifying cardiac complexes sensed during an arrhythmic episode. Additional morphology analysis techniques include amplitude distribution analysis and spectral analysis. Other morphology analysis techniques are known and are considered to be with the scope of the present subject matter.

By initially aligning the cardiac complex detected in the first signal with the first NSR representative complex, the time the cardiac complex detected in the second signal and the second NSR representative complex occurred relative the first signal with the first NSR representative complex become a factor in determining what portion of the second NSR representative complex is compared to the cardiac complex in the second signal.

FIGS. 8A and 8B show one embodiment of aligning the cardiac complex detected in the first signal with the first NSR representative complex. In 800 of FIG. 8B there is shown a window containing a cardiac complex detected in a first signal 804 and a second signal 808. In one embodiment, the first signal 804 is a near-field signal of an R-wave, and the second signal 808 is a far-field signal of a QRS-cardiac complex. In 812 of FIG. 8A there is shown a window containing a first NSR representative complex 816 and a second NSR representative complex 820. In the present example, the first NSR representative complex 816 is a near-field signal of an R-wave, and the second NSR representative complex 820 is a far-field signal of a QRS-cardiac complex.

Figure 9A:
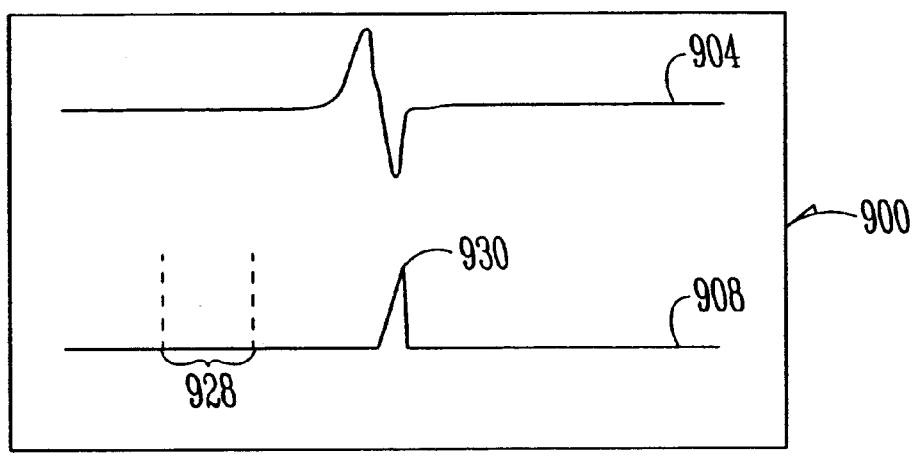
FIGS. 9A and 9B show one embodiment of aligning cardiac complexes according to the present subject matter.
Figure 9B:
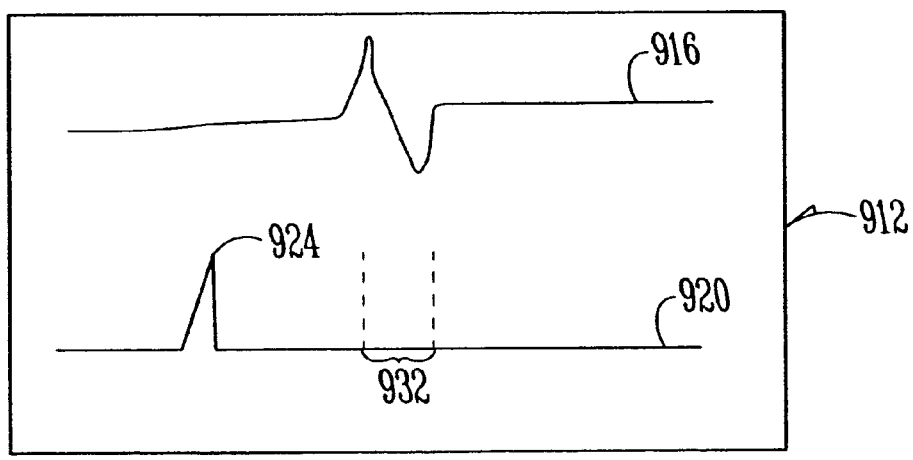

As previously discussed, the morphology analyzer circuit 648 locates the predetermined feature in the cardiac complex detected in the first signal 804 and in the first NSR representative complex 816. The signal feature comparison circuit 638 then aligns the predetermined feature in the cardiac complex monitored in the first signal 804 with the predetermined feature on the first NSR representative complex 816. In FIGS. 8A and 8B, the cardiac complex 800 and the first NSR representative complex 812 are aligned around a maximum deflection 824 of the cardiac complexes 804 and 816. The signal feature comparison circuit 638 then compares the cardiac complex monitored in the second signal 808 to the second NSR representative complex 820 to determine whether the cardiac complex is an arrhythmic complex. As previously discussed, because the predetermined feature in the cardiac complex monitored in the first signal 804 has been aligned with the predetermined feature on the first NSR representative complex 816, the time the second signal 808 occurs relative the first signal 804 and the time the second NSR representative complex 820 occurs relative the first NSR representative complex 816 can be used to accentuate morphological differences between the complexes. So in one embodiment, the QRS-cardiac complex 828 in the second signal 808 is morphologically compared to a region 832 along the second NSR representative complex 820. Alternatively, the QRS-cardiac complex 834 in the second NSR representative complex 820 is morphologically compared to a region 836 along the second signal 808. 'FIGS. 9A and 9B show an alternative embodiment of aligning a cardiac complex sensed during a tachycardia episode with a normal sinus rhythm template cardiac complex. In 900 of FIG. 9A there is shown a window of a first NSR representative complex 904 and a second NSR representative complex 908. In the present example, the first NSR representative complex 904 is a far-field signal of a QRS-cardiac complex, and the second NSR representative complex 908 is a near-field signal of an R-wave cardiac complex. In 912 of FIG. 9B there is shown a window of a cardiac complex sensed during a tachycardia episode, where the first signal 916 is a far-field signal of a QRS-cardiac complex and the second signal 920 is a near-field signal of an R-wave cardiac complex.

In the present embodiment, the cardiac complex 912 and the representative NSR complex 900 are aligned around the beginning, or the start, of the cardiac complexes 904 and 916. After the representative NSR complex and the tachycardiac cardiac complex have been aligned, the morphology of the second signal 920 is compared to the morphology of the second NSR representative complex 908 to determine whether the cardiac complex is an arrhythmic complex. In one embodiment, the R-wave cardiac complex 924 in the second signal 920 is morphologically compared to a region 928 along the second NSR representative complex 908. In an alternative embodiment, the R-wave cardiac complex 930 in the second NSR representative complex 908 is morphologically compared to a region 932 along the second signal 920.

In one embodiment, the present subject matter can classify a variety of cardiac complexes, including VT-complexes, SVT-complexes and NSR-complexes. Other classifications for the tachycardiac cardiac complex are known and are considered within the scope of the present invention.

Figure 10:
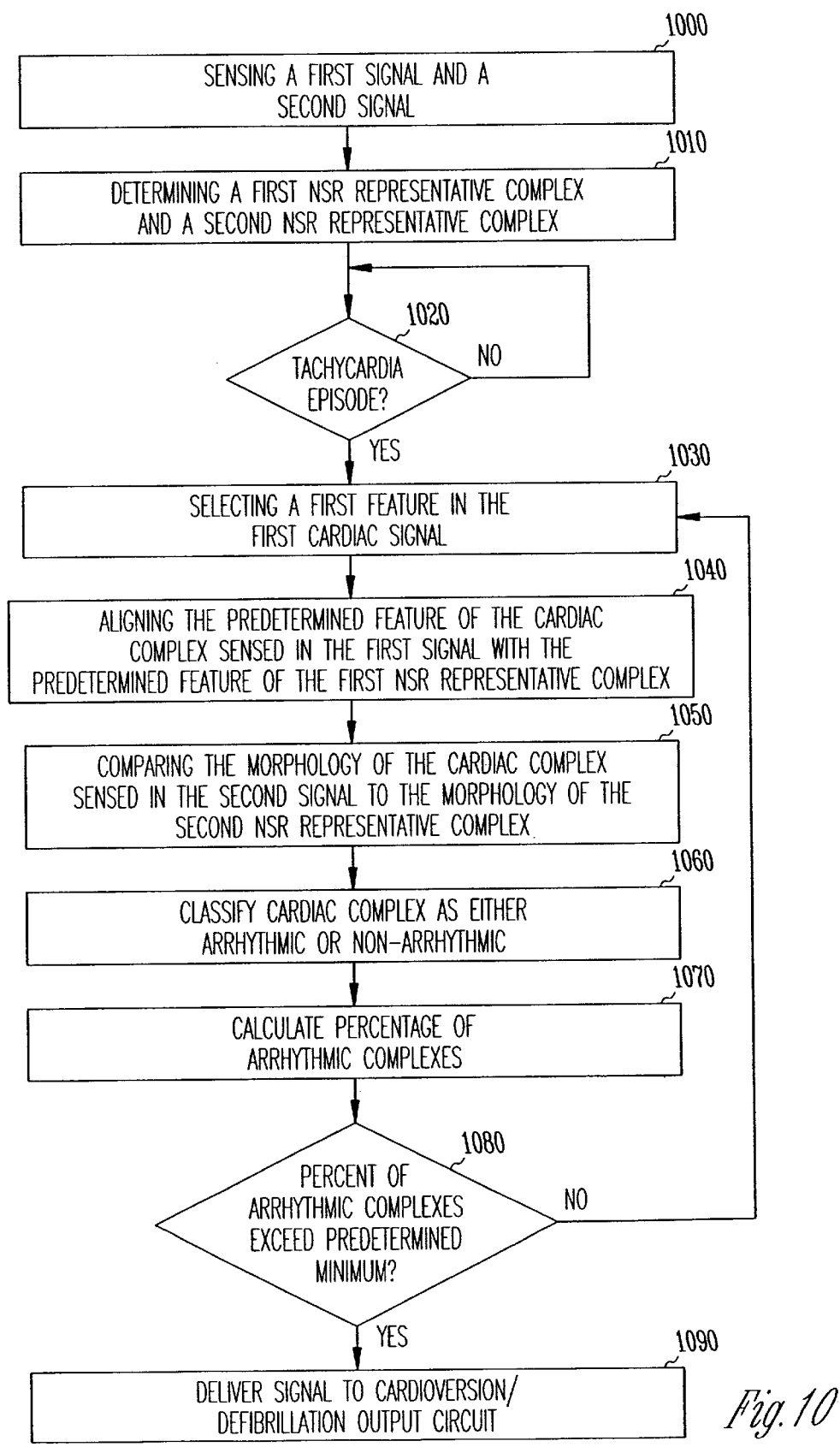
FIG. 10 is a flow diagram illustrating one embodiment of the present subject matter.

FIG. 10 shows an additional embodiment of the present subject matter. At 1000, a first signal and a second signal representative of electrical cardiac activity are sensed from a patient. In one embodiment, each of the signals include cardiac complexes representative of cardiac cycles. At 1010, a plurality normal sinus rhythm (NSR) cardiac complexes are detected in the first signal and the second signal. In one embodiment, the medical device system determines the first NSR representative complex from the plurality of NSR cardiac complexes detected in the first signal and determines the second NSR representative complex from the plurality of NSR cardiac complexes detected in the second signal. The first and second NSR representative complexes are then stored in the memory of the medical device system.

At 1020, cardiac complexes monitored in at least the first signal are analyzed by the medical device system to detect the onset of a tachycardia episode. If no tachycardia episode is detected, the system continues to sense cardiac signals and analyzes them for the occurrence of a tachycardia episode. In one embodiment, the occurrence of a tachycardia episode is based on the cardiac rate, where a tachycardia episode is declared when the cardiac rate exceeds a predetermined threshold. In one embodiment, the predetermined threshold is a cardiac rate of between 150 and 180 beats per minute. Other systems of determining the occurrence of a tachycardia episode are known and are considered to be within the scope of the present system.

When a tachycardia episode is detected the system then proceeds to 1030. At 1030, the first signal and the second signal are monitored for the occurrence of cardiac complexes. The detected cardiac complexes are analyzed, or processed, so that each cardiac complex is classified as either an arrhythmic complex or a non-arrhythmic complex. In processing each cardiac complex at 1030, the predetermined feature is located in the cardiac complex detected in the first signal and the first NSR representative complex. As previously discussed, the predetermined feature includes a repeatably identifiable portion of cardiac complexes.

At 1040, the predetermined feature on the cardiac complex sensed in the first signal is then aligned with the corresponding first feature found on the first NSR representative complex. In one embodiment, the predetermined feature on the first NSR representative complex has been previously located and stored in the memory of the medical device system. After the predetermined feature on both the cardiac complex sensed in the first signal and the first NSR representative complex have been aligned, the cardia complex sensed in the second signal is compared to the second NSR representative complex at 1050. In one embodiment, the second NSR representative complex has a second NSR morphology and the cardiac complex detected in the second signal has a second signal morphology, where the second NSR morphology is compared to the second signal morphology to determine whether the cardia complex is an arrhythmic complex. Based on the comparison, the cardiac complex is classified as either an arrhythmic complex or as a non-arrhythmic complex at 1060.

After making a determination as to whether a cardiac complex is an arrhythmic complex or a non-arrhythmic complex, a percentage of arrhythmic complexes is determined at 1070. At 1080, the calculated percentage of arrhythmic complexes is compared to a predetermined percentage threshold. In one embodiment, therapy for treating the condition associated with the arrhythmic complexes being sensed is applied to the patient's heart at 1090 when the percentage of arrhythmic complexes exceeds the predetermined percentage threshold. If the percentage of arrhythmic complexes does not exceed the predetermined percentage threshold, the system returns to 1030. In one embodiment, the predetermined percentage threshold is a programmable value in the range of 40 to 60 percent, where a value of approximately 50 percent is an acceptable value.

Figure 11:
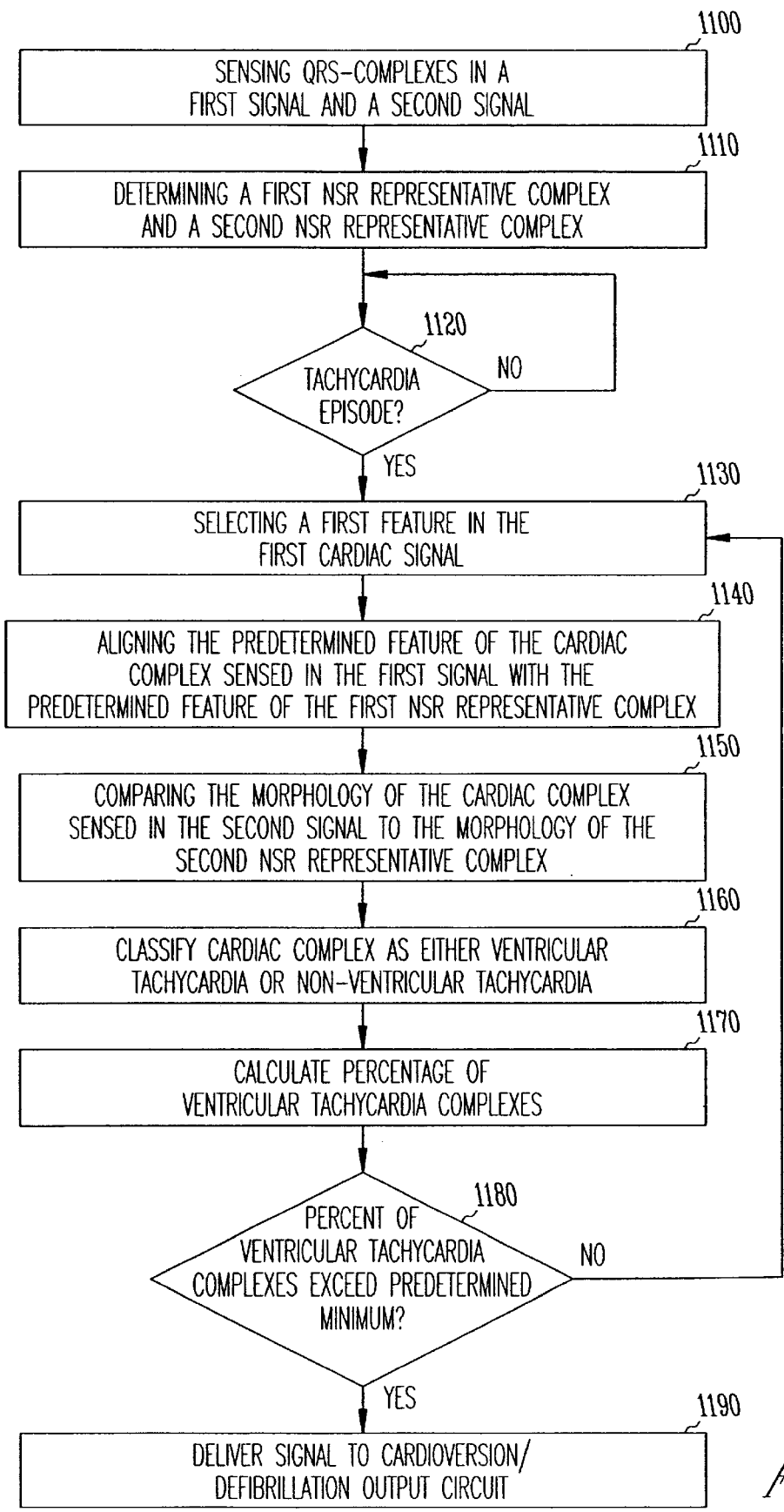
FIG. 11 is a flow diagram illustrating one embodiment of the present subject matter.

FIG. 11 shows an additional embodiment of the present subject matter. At 1100, a first signal and a second signal representative of electrical cardiac activity are sensed from a patient, where the first signal and the second signal each include at least a portion of a QRS-complex. At 1110, a plurality normal sinus rhythm (NSR) cardiac complexes are detected in the first signal and the second signal. The medical device system determines the first NSR representative complex from the at least a portion of the QRS-complex in each of the plurality of NSR cardiac complexes detected in the first signal and the second NSR representative complex from the at least a portion of the QRS-complex in each of the plurality of NSR cardiac complexes detected in the second signal. The first and second NSR representative complexes are then stored in the memory of the medical device system.

At 1120, cardiac complexes monitored in at least the first signal are analyzed by the medical device system to detect the onset of a tachycardia episode. If no tachycardia episode is detected the system continues to sense cardiac signals and analyzes them for the occurrence of a tachycardia episode. In one embodiment, the occurrence of a tachycardia episode is based on the ventricular cardiac rate, where a tachycardia episode is declared when the ventricular cardiac rate exceeds a predetermined threshold. In one embodiment, the predetermined threshold is a ventricular cardiac rate of between 150 and 180 beats per minute. Other systems of determining the occurrence of a tachycardia episode are known and are considered to be within the scope of the present system.

When a tachycardia episode is detected the system then proceeds to 1130. At 1130, the first signal and the second signal are monitored for the occurrence of cardiac complexes. The detected cardiac complexes are analyzed, or processed, so that each cardiac complex is classified as either a ventricular tachycardia complex or a non-ventricular tachycardia complex. In processing each cardiac complex at 1130, the predetermined feature is located in the cardiac complex detected in the first signal and the first NSR representative complex. As previously discussed, the predetermined feature includes a repeatably identifiable portion of cardiac complexes.

At 1140, the predetermined feature on the cardiac complex sensed in the first signal is then aligned with the corresponding first feature found on the first NSR representative complex. In one embodiment, the predetermined feature on the first NSR representative complex has been previously located and stored in the memory of the medical device system. After the predetermined feature on both the cardiac complex sensed in the first signal and the first NSR representative complex have been aligned, the cardia complex sensed in the second signal is compared to the second NSR representative complex at 1150. In one embodiment, the second NSR representative complex has a second NSR morphology and the cardiac complex detected in the second signal has a second signal morphology, where the second NSR morphology is compared to the second signal morphology to determine whether the cardia complex is a ventricular tachycardia complex or a non-ventricular tachycardia complex. Based on the comparison, the cardiac complex is classified as either a ventricular tachycardia complex or a non-ventricular tachycardia complex at 1160.

After making a determination as to whether a cardiac complex is a ventricular tachycardia complex or a non-ventricular tachycardia complex, a percentage of ventricular tachycardia complexes is determined at 1170. At 1180, the calculated percentage of ventricular tachycardia complexes is compared to a predetermined percentage threshold. In one embodiment, therapy for treating a ventricular tachycardia is applied to the patient's heart at 1190 when the percentage of ventricular tachycardia complexes exceeds the predetermined percentage threshold. If the percentage of ventricular tachycardia complexes does not exceed the predetermined percentage threshold, the system returns to 1130. In one embodiment, the predetermined percentage threshold is a programmable value in the range of 40 to 60 percent, where a value of approximately 50 percent is an acceptable value.

Figure 12:
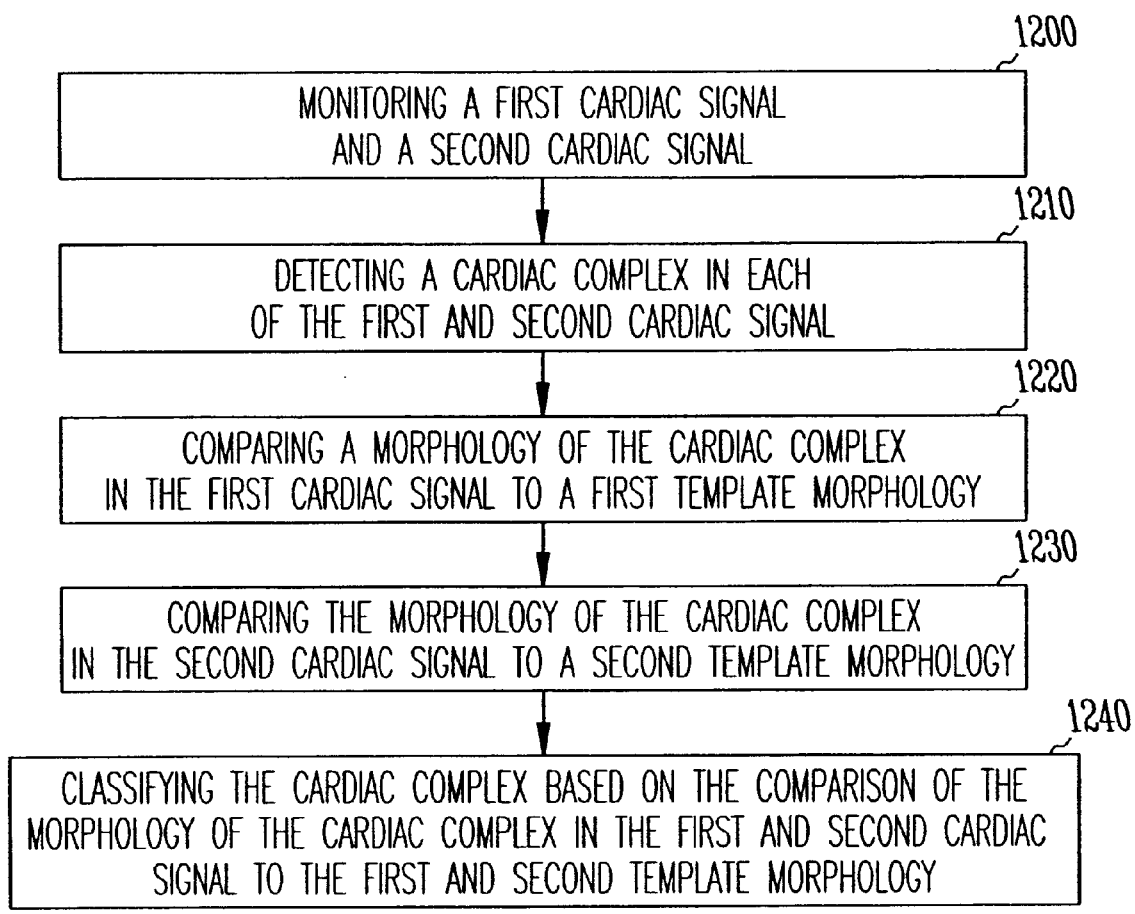
FIG. 12 is a flow diagram illustrating one embodiment of the present subject matter.

FIG. 12 shows an additional embodiment of the present subject matter. At 1200, a first cardiac signal and a second cardiac signal representative of electrical cardiac activity are sensed and monitored from a patient. In one embodiment, the first cardiac signal and the second cardiac signal are monitored from a first cardiac region and a second cardiac region, respectively. At 1210, cardiac complexes are detected in the first cardiac signal and the second cardiac signal. As the cardiac complexes are sensed, template morphologies are developed for cardiac conditions exhibited by the patient. In one embodiment, as the patient experiences a cardiac condition (such as a ventricular tachycardia or supraventricular tachycardia) the cardiac complexes are recorded. In one embodiment, the system can then use the recorded cardiac complexes to develop a template morphology for the cardiac condition.

In one embodiment, the template morphology is comprised of a first template morphology and a second template morphology. In one embodiment, the first template morphology is derived from cardiac complexes monitored in the first cardiac signal sensed from approximately the first cardiac region and the second template morphology is derived from cardiac complexes monitored in the second cardiac signal sensed from approximately the second cardiac region. In an alternative embodiment, the first template morphology and the second template morphology for each cardiac condition of interest are developed through groups of patient data and programmed into the memory of the medical device system. The template cardiac complexes are then stored in the memory of the medical device system.

In one embodiment, the patient's cardiac complexes are monitored and analyzed by the medical device system. In one embodiment, the cardiac complexes are monitored for the onset of a tachycardia event. In an alternative embodiment, the cardiac complexes are monitored to detect the occurrence of a predetermined class or type of cardiac complex (e.g., PVCs, ischemic complexes). In one embodiment, to determine the occurrence of the predetermined class of cardiac complexes, the cardiac complexes sensed in the cardiac signals are morphologically compared to the template cardiac complexes.

For the present embodiment, the morphology of the cardiac complex in the first cardiac signal is compared to the first template morphology at 1220. At 1230, the morphology of the cardiac complex in the second cardiac signal is compared to the second template morphology of a cardiac condition template morphology. Based on the comparison, the sensed cardiac complexes are then classified as either belonging to or not belonging to one or more of the classes of cardiac complexes represented by the template cardiac complexes at 1240. After classifying each cardiac complex, the medical device system can retain the sensed cardiac complexes in memory. In addition, a percentage of the classified complexes is determined at 1070.

In an additional embodiment, a third cardia signal containing the cardiac complex can be monitored. A third template morphology can be developed in the same manner as described for the first and second template morphologies. The morphology of the cardiac complex in the third cardiac signal is then compared to a third template morphology. So, the cardiac complex can be classified based on the comparison of the morphology of the cardiac complex in the first cardiac signal, the second cardiac signal and the third cardiac signal to the first template morphology, the second template morphology and the third template morphology.

What is claimed is:

1. A method, comprising:
   monitoring a first cardiac signal and a second cardiac signal;
   detecting a first cardiac complex in the first cardiac signal and a second cardiac complex in the second cardiac signal, the first and second cardiac complexes associated with the same heart contraction;
   creating at least one first template cardiac complex for the first cardiac signal and at least one second template cardiac complex for the second cardiac signal, wherein each of the first and second template cardiac complexes represents a predetermined cardiac rhythm state;
   comparing the first cardiac complex to the first template cardiac complex and the second cardiac complex to the second template cardiac complex to determine whether the heart contraction is representative of the predetermined cardiac rhythm state; and
   classifying the heart contraction as being representative of the predetermined cardiac rhythm state based on the comparison of the first cardiac complex to the first template cardiac complex and the second cardiac complex to the second template cardiac complex.

2. The method of claim 1, further comprising determining a therapy at least in part in response to the classification of the heart contraction.

3. The method of claim 2, furthering comprising delivering, at least in part in response to the classification of the heart contraction, at least one of:
   a cardiac pacing therapy;
   a cardioversion therapy; and
   a defibrillation therapy.

4. The method of claim 1, wherein the predetermined cardiac rhythm state includes at least one of:
   a normal sinus rhythm (NSR);
   a ventricular tachycardia (VT);
   a supraventricular tachycardia (SVT);
   a premature ventricular contraction (PVC); and
   an ischemic event.

5. The method of claim 1, wherein the first and second template cardiac complexes are template morphologies and comparing the first and second cardiac complexes to the corresponding first and second template cardiac complexes comprises comparing morphologies of the first and second cardiac complexes to the respective first and second template morphologies.

6. The method of claim 5, further comprising deriving the first and second template morphologies from cardiac complexes detected in the first and second cardiac signals, respectively.

7. The method of claim 6, wherein the first and second template morphologies are each derived from at least one repeatably identifiable feature of cardiac complexes sensed from a patient manifesting at least one of the predetermined cardiac rhythm states.

8. The method of claim 6, wherein the first and second template morphologies are each derived from at least one repeatably identifiable feature of cardiac complexes sensed from a population of patients manifesting at least one of the predetermined cardiac rhythm states.

9. The method of claim 5, wherein comparing the morphologies comprises comparing at least one predetermined feature in the first and second cardiac complexes to a corresponding at least one predetermined feature in the corresponding one of the first and second template morphologies.

10. The method of claim 9, wherein the predetermined feature includes at least one of:
   a maximum signal deflection;
   a predetermined signal deviation from a baseline; and
   a signal return to the baseline for a predetermined time period.

11. The method of claim 10, further comprising aligning the predetermined feature in the first and second cardiac complexes and the respective first and second morphologies.

12. The method of claim 11, furthering comprising utilizing a correlation waveform analysis algorithm for comparing the first and second cardiac complexes to the respective first and second morphologies.

13. A method, comprising:
   monitoring a first cardiac signal and a second cardiac signal;
   detecting a first cardiac complex in the first cardiac signal and a second cardiac complex in the second cardiac signal, the first and second cardiac complexes associated with the same heart contraction;
   locating at least one first predetermined feature in the first cardiac complex and at least one second predetermined feature in the second cardiac complex;
   generating at least one characteristic quantity as a function of a position of at least one of the first and second predetermined features; and
   classifying the heart contraction as being representative of a predetermined cardiac rhythm state based at least in part on the characteristic quantity.

14. The method of claim 13, further comprising determining a therapy at least in part in response to the classification of the heart contraction.

15. The method of claim 14, furthering comprising delivering, at least in part in response to the classification of the heart contraction, at least one of:
   a cardiac pacing therapy;
   a cardioversion therapy; and
   a defibrillation therapy.

16. The method of claim 13, wherein the cardiac signals are monitored to provide a substantially simultaneous view of a cardiac complex from at least two different cardiac locations.

17. The method of claim 13, wherein the predetermined cardiac rhythm state includes at least one of:
   a normal sinus rhythm (NSR);
   a ventricular tachycardia (VT);
   a supraventricular tachycardia (SVT);
   a premature ventricular contraction (PVC); and
   an ischemic event.

18. The method of claim 13, wherein at least one of the first and second predetermined features is at least one of:
   a maximum signal deflection;
   a predetermined signal deviation from a baseline; and
   a signal return to the baseline for a predetermined time period.

19. The method of claim 13, further comprising:
   creating at least one classification quantity, wherein the classification quantity represents a predetermined cardiac rhythm state; and
   comparing the characteristic quantity to the classification quantity to determine whether the characteristic quantity is representative of the predetermined cardiac rhythm state;
   wherein the classifying the heart contraction is based at least in part on the outcome of the comparing the characteristic quantity to the classification quantity.

20. The method of claim 19, wherein the characteristic quantity comprises a characteristic scalar value, the classification quantity comprises a classification scalar value, and the comparing the characteristic quantity to the classification quantity comprises comparing the characteristic scalar value to the classification scalar value.

21. The method of claim 20, further comprising deriving the classification scalar value from cardiac complexes detected in the first and second cardiac signals.

22. The system of claim 19, wherein the characteristic scalar value is representative, at least in part, of at least one of:
   a time associated with at least one of the first and second predetermined features;
   a time difference between the first and second predetermined features;
   an amplitude value of at least one of the first and second predetermined features; and
   a time difference between two predetermined features in one cardiac signal.

23. The method of claim 19, wherein the classification scalar value is population-based.

24. The method of claim 19, wherein the classification scalar value is individual-based.

25. The method of claim 19, wherein:
   the characteristic quantity is a characteristic vector comprising two or more scalar values;
   the classification quantity is a classification vector; and
   comparing the characteristic quantity to the classification quantity comprises comparing the characteristic vector to the classification vector.

26. The method of claim 25, wherein classifying the heart contraction comprises:
   determining a correlation between the characteristic vector and the classification vector; and
   classifying the cardiac complex as being representative of the predetermined cardiac rhythm state if the correlation exceeds a predetermined threshold.

27. The method of claim 26, wherein determining the correlation comprises determining a mean square error value between the characteristic vector and the classification vector.

28. A system, comprising
   an amplifier to sense first and second cardiac signals;
   a detector, coupled to the amplifier, to detect first and second cardiac complexes in the respective first and second cardiac signals, the first and second cardiac complexes associated with the same heart contraction;
   a morphology analyzer, coupled to the detector, to locate at least one predetermined feature in a morphology of each of the first and second cardiac complexes;
   a comparator, coupled to the morphology analyzer, to compare the first and second cardiac complexes with respective first and second template cardiac complexes; and
   a processor, coupled to the comparator, to classify the heart contraction.

29. The system of claim 28, wherein the predetermined feature includes at least one of:
- a maximum signal deflection;
- a predetermined signal deviation from a baseline; and
- a signal return to the baseline for a predetermined time period.

30. The system of claim 29, wherein the morphology analyzer further comprises at least one scalar value that is representative, at least in part, of at least one of:
- a time associated with at least one of the first and second predetermined features;
- a time difference between the first and second predetermined features;
- an amplitude value of at least one of the first and second predetermined features; and
- a time difference between two predetermined features in one cardiac signal.

31. The system of claim 29, further comprising a template generator, coupled to the comparator, to generate at least one template morphology for each of the first and second cardiac signals, wherein the template morphology represents a predetermined cardiac rhythm state that includes at least one of:
- a normal sinus rhythm (NSR);
- a ventricular tachycardia (VT);
- a supraventricular tachycardia (SVT);
- a premature ventricular contraction (PVC); and
- an ischemic event.

32. The system of claim 31, wherein the template generator comprises a characterization vector comprising at least two scalar values.

33. The system of claim 28, further comprising a cardiac rhythm analyzer, coupled to the amplifier, to analyze at least one of the first and second cardiac signals to detect a predetermined cardiac condition.

34. The system of claim 33, wherein the cardiac rhythm analyzer comprises a heart rate detector.

35. The system of claim 28, wherein the comparator includes a correlation waveform analysis algorithm to compare the morphologies of the first and second cardiac complexes with respective first and second template morphologies.

36. The system of claim 28, wherein the comparator comprises comparing a characteristic quantity to a classification quantity.

37. The system of claim 36, wherein the comparator comprises comparing a characteristic scalar value to a classification scalar value.

38. The system of claim 36, wherein the comparator comprises comparing a characteristic vector to a classification vector, wherein the characteristic vector comprises at least two scalar values and the classification vector comprises at least two scalar values.

39. The system of claim 28, further comprising a therapy delivery circuit, wherein the therapy delivery circuit comprises at least one of:
- a pace output circuit; and
- a cardioversion and defibrillation output circuit.

* * * * *